US006060326A

United States Patent [19]
Frank et al.

[11] Patent Number: 6,060,326
[45] Date of Patent: May 9, 2000

[54] METHOD TO DETECT CANINE IGE AND KIT THEREFOR

[75] Inventors: Glenn R. Frank, Wellington; Keith E. Rushlow, Fort Collins, both of Colo.

[73] Assignee: Heska Corporation, Fort Collins, Colo.

[21] Appl. No.: 08/833,488

[22] Filed: Apr. 7, 1997

[51] Int. Cl.$^7$ .................. G01N 33/563; G01N 33/53; G01N 33/567; C12Q 1/68
[52] U.S. Cl. .................. 436/513; 435/6; 435/7.1; 435/7.21; 435/7.3; 435/7.31; 435/7.32; 435/7.5; 435/7.93; 435/7.94; 435/7.95; 435/970; 436/518; 436/808
[58] Field of Search .................. 435/6, 7.1, 7.21, 435/7.3, 7.31, 7.32, 7.5, 7.93–7.95, 970; 436/513, 518, 808

[56] References Cited

U.S. PATENT DOCUMENTS

| | | | |
|---|---|---|---|
| 4,849,337 | 7/1989 | Calenoff et al. | 435/7.9 |
| 4,962,035 | 10/1990 | Leder et al. | 435/320 |
| 4,968,633 | 11/1990 | Marcucci | 436/513 |
| 5,091,318 | 2/1992 | Anawis et al. | 436/513 |
| 5,424,193 | 6/1995 | Pronovost et al. | 435/7.32 |
| 5,625,039 | 4/1997 | Washida et al. | 530/388.25 |
| 5,629,415 | 5/1997 | Hollis et al. | 536/23.53 |
| 5,714,338 | 2/1998 | Wai Fei et al. | 435/7.24 |

FOREIGN PATENT DOCUMENTS

| | | | |
|---|---|---|---|
| 550 020 A2 | 7/1993 | European Pat. Off. | 530/388.25 |
| WO 90/04640 | 5/1990 | WIPO . | |
| WO 91/06570 | 5/1991 | WIPO . | |

OTHER PUBLICATIONS

Derwent Abstract WPI Acc No: 93–185519/23, Toray Ind. Inc, "JP 5113443" from Dialog Database, File 351.

Kochan, et al., "Isolation of the Gene Coding for the Alpha Subunit of the Human High Affinity IgE Receptor," (1988) *Nucleic Acids Res. 16(8)*, p. 3584.

Küster, et al., "Characterization and Expression of the Gene for the Human Fc Receptor γ Subunit," (1990) *J. Biol. Chem. 265(11)*, pp. 6448–6452.

Küster, et al., "The Gene and cDNA for the Human High Affinity Immunoglobulin E Receptor β Chain and Expression of the Complete Human Receptor," (1992) *J. Biol. Chem. 267(18)*, pp. 12782–12787.

Lowenthal, et al., "Passive Transfer of IgE–Mediated Cutaneous Reactivity in Heterologous Species," (1993) *Annals of Allergy 71*, pp. 481–484.

Pang, et al., "Characterization of the Gene for the Human High Affinity IgE Receptor (FcεRI) α–Chain," (1993) *J. Immunol. 151(11)*, pp. 6166–6174.

Shimizu, et al., "Human and Rat Mast Cell High–Affinity Immunoglobulin E Receptors: Characterization of Putative α–Chain Gene Products," (1988), *Proc. Natl. Acad. Sci. USA (85)*, pp. 1907–1911.

Nakamura et al., *Handbook of Experimental Immunology in Four volumes. vol. 1: Immunochemistry*, Ed. D.M. Weir, Chapter 27, pp. 27.1–27.20, Jan. 1987.

Suto et al., "Detection of Human High Affinity IgE Receptor (FcεRI)–bindable IgE in Sera of Patients with Atopic Dermatitis: A Novel Enzyme–linked Immunosorbent Assay (ELISA) Using a Recombinant Soluble form of the Human FcεRIα Chain," (1996) *Jpn J. Dermatol 106*, pp. 1377–1384. Japanese with English Abstract.

Hayashi et al., Genbank Accession No. D16413, submitted Jun. 8, 1993.

*Primary Examiner*—James C. Housel
*Assistant Examiner*—Gailene R. Gabel
*Attorney, Agent, or Firm*—Heska Corporation

[57] ABSTRACT

The present invention includes a method to detect canine IgE using a canine Fc epsilon receptor ($Fc_\epsilon R$) to detect canine IgE antibodies in a biological sample from a canid. The present invention also relates to kits to perform such methods.

38 Claims, No Drawings

METHOD TO DETECT CANINE IGE AND KIT THEREFOR

FIELD OF THE INVENTION

The present invention relates to a novel method to detect canine epsilon immunoglobulin (IgE). The present invention also includes novel kits to detect canine IgE as well as methods to produce the detection reagent.

BACKGROUND OF THE INVENTION

Diagnosis of disease and determination of treatment efficacy are important tools in medicine. In particular, detection of IgE production in an animal can be indicative of disease. Such diseases include, for example, allergy, atopic disease, hyper IgE syndrome, internal parasite infections and B cell neoplasia. In addition, detection of IgE production in an animal following a treatment is indicative of the efficacy of the treatment, such as when using treatments intended to disrupt IgE production.

Until the discovery of the present invention, detection of IgE in samples obtained from non-human animals has been hindered by the absence of suitable reagents for detection of IgE. Various compounds have been used to detect IgE in IgE-containing compositions. In particular, antibodies that bind selectively to epsilon idiotype antibodies (i.e., anti-IgE antibodies) have been used to detect IgE. These anti-IgE antibodies, however, can cross-react with other antibody idiotypes, such as gamma isotype antibodies. The discovery of the present invention includes the use of a canine Fc epsilon receptor ($Fc_\epsilon R$) molecule to detect the presence of IgE in a putative IgE-containing composition. Canine high affinity $Fc_\epsilon R$ consists of three protein chains, alpha, beta and gamma. Hayashi et al. have disclosed the nucleic acid sequence for the alpha chain (GenBank Accession No. D16413, submitted Jun. 8, 1993). A canine $Fc_\epsilon R$ molecule provides an advantage over, for example anti-IgE antibodies, to detect IgE because a canine $Fc_\epsilon R$ molecule can bind to a canine IgE with more specificity (i.e., less idiotype cross-reactivity) and more sensitivity (i.e., affinity) than anti-IgE binding antibodies.

Thus, methods and kits are needed in the art that will provide specific detection of canine IgE using canine $Fc_\epsilon R$.

SUMMARY OF THE INVENTION

The present invention includes detection methods and kits that detect canine IgE.

One embodiment of the present invention is a method to detect canine IgE comprising: (a) contacting an isolated canine $Fc_\epsilon$ receptor ($Fc_\epsilon R$) molecule with a putative canine IgE-containing composition under conditions suitable for formation of a $Fc_\epsilon R$ molecule:IgE complex; and (b) determining the presence of IgE by detecting the $Fc_\epsilon R$ molecule:IgE complex, the presence of the $Fc_\epsilon R$ molecule:IgE complex indicating the presence of IgE. In particular, the canine $Fc_\epsilon R$ molecule comprises at least a portion of a $Fc_\epsilon R$ alpha chain that binds to canine IgE.

Another embodiment of the present invention is a method to detect canine flea allergy dermatitis comprising: (a) immobilizing a flea allergen on a substrate; (b) contacting the flea allergen with a putative canine IgE-containing composition under conditions suitable for formation of an antigen:IgE complex bound to the substrate; (c) removing non-bound material from the substrate under conditions that retain antigen:IgE complex binding to the substrate; and (d) detecting the presence of the antigen:IgE complex by contacting antigen:IgE complex with a canine $Fc_\epsilon R$ molecule. In particular, the flea allergen is a flea saliva antigen.

The present invention also includes a kit for performing methods of the present invention. One embodiment is a kit for detecting IgE comprising a canine $Fc_\epsilon$ receptor ($Fc_\epsilon R$) molecule and a means for detecting canine IgE. Another embodiment is a kit for detecting flea allergy dermatitis comprising a canine $Fc_\epsilon$ receptor ($Fc_\epsilon R$) molecule and a flea allergen.

DETAILED DESCRIPTION OF THE INVENTION

The present invention relates to the discovery that purified high affinity canine Fc epsilon receptor (i.e., $Fc_\epsilon RI$; referred to herein as $Fc_\epsilon R$) can be used in canine epsilon immunoglobulin (referred to herein as IgE or IgE antibody)-based detection (e.g., diagnostic, screening) methods and kits. The use of canine $Fc_\epsilon R$ in diagnostic methods and kits is unexpected because the use of canine $Fc_\epsilon R$ avoids complications presented by use of antibodies that bind to IgE (i.e., anti-IgE antibodies). Such complications include, for example, non-specific binding of anti-IgE antibodies to other classes of immunoglobulin such as gamma immunoglobulin (i.e., IgG).

One embodiment of the present invention is a method to detect a canine IgE using an isolated canine $Fc_\epsilon R$ molecule. It is to be noted that the term "a" entity or "an" entity refers to one or more of that entity; for example, a protein refers to one or more proteins or at least one protein. As such, the terms "a" (or "an"), "one or more" and "at least one" can be used interchangeably herein. It is also to be noted that the terms "comprising", "including", and "having" can be used interchangeably. Furthermore, a compound "selected from the group consisting of" refers to one or more of the compounds in the list that follows, including mixtures (i.e., combinations) of two or more of the compounds.

According to the present invention, an isolated, or biologically pure, $Fc_\epsilon R$ molecule, is a molecule that has been removed from its natural milieu. As such, "isolated" and "biologically pure" do not necessarily reflect the extent to which the molecule has been purified. An isolated canine $Fc_\epsilon R$ molecule of the present invention can be obtained from its natural source (e.g., from a canine mast cell), can be produced using recombinant DNA technology or can be produced by chemical synthesis.

A $Fc_\epsilon R$ molecule (also referred to herein as $Fc_\epsilon R$ or $Fc_\epsilon R$ protein) of the present invention can be a full-length protein, a portion of a full-length protein or any homolog of such a protein, wherein the $Fc_\epsilon R$ molecule is capable of binding specifically to IgE. As used herein, a protein can be a polypeptide or a peptide. A $Fc_\epsilon R$ molecule of the present invention can comprise a complete $Fc_\epsilon R$ (i.e., alpha, beta and gamma $Fc_\epsilon R$ chains), an alpha $Fc_\epsilon R$ chain (also referred to herein as $Fc_\epsilon R$ α chain) or portions thereof. Preferably, a $Fc_\epsilon R$ molecule comprises at least a portion of a $Fc_\epsilon R$ α chain that binds to IgE, i.e., that is capable of forming an immunocomplex with an IgE constant region.

An isolated canine $Fc_\epsilon R$ molecule of the present invention, including a homolog, can be identified in a straight-forward manner by the $Fc_\epsilon R$ molecule's ability to form an immunocomplex with a canine IgE. Examples of $Fc_\epsilon R$ homologs include $Fc_\epsilon R$ proteins in which amino acids have been deleted (e.g., a truncated version of the protein, such as a peptide), inserted, inverted, substituted and/or derivatized (e.g., by glycosylation, phosphorylation, acetylation, myristoylation, prenylation, palmitoylation, amidation and/or addition of glycerophosphatidyl inositol) such that the homolog includes at least one epitope capable of forming an immunocomplex with an IgE.

$Fc_\epsilon R$ homologs can be the result of natural allelic variation or natural mutation. $Fc_\epsilon R$ homologs of the present invention can also be produced using techniques known in the art including, but not limited to, direct modifications to the protein or modifications to the gene encoding the protein using, for example, classic or recombinant DNA techniques to effect random or targeted mutagenesis.

According to the present invention, a preferred canine $Fc_\epsilon R$ α chain of the present invention is encoded by at least a portion of the nucleic acid sequence of the coding strand of a cDNA encoding a full-length $Fc_\epsilon R$ α chain protein represented herein as SEQ ID NO: 19, the portion at least encoding the IgE binding site of the $Fc_\epsilon R$ α chain protein. Other suitable canine $Fc_\epsilon R$ α chains useful in the present invention include those described herein in the Examples section. The double-stranded nucleic acid molecule including both the coding strand having SEQ ID NO: 19 and the complementary non-coding strand (the nucleic acid sequence of which can be readily determined by one skilled in the art and is shown herein as SEQ ID NO: 21) is referred to herein as $Fc_\epsilon R$ nucleic acid molecule $ncFc_\epsilon R\alpha4_{991}$. Translation of SEQ ID NO: 19 suggests that nucleic acid molecule $ncFc_\epsilon R\alpha4_{991}$, encodes a full-length $Fc_\epsilon R$ α chain protein of about 253 amino acids, referred to herein as $PcFc_\epsilon R\alpha4_{253}$, represented by SEQ ID NO: 20, assuming an open reading frame having an initiation (start) codon spanning from about nucleotide 35 through about nucleotide 37 of SEQ ID NO: 19 and the termination codon spans from about nucleotide 793 through about nucleotide 795 of SEQ ID NO: 19. The coding region encoding $PcFc_\epsilon R\alpha4_{253}$, excluding the stop codon, is represented by nucleic acid molecule $ncFc_\epsilon R\alpha4_{759}$, having a coding strand with the nucleic acid sequence represented by SEQ ID NO: 22 and a complementary strand with nucleic acid sequence SEQ ID NO: 23. SEQ ID NO: 19 encodes a signal peptide spanning from about amino acid 1 through about amino acid 24, as well as a mature protein of about 229 amino acids, denoted herein as $PcFc_\epsilon R\alpha4_{229}$, the amino acid sequence of which is represented herein as SEQ ID NO: 24. The nucleic acid molecule encoding the apparent mature protein is referred to as $ncFc_\epsilon R\alpha4_{687}$, the nucleic acid sequence of the coding strand of which is denoted herein as SEQ ID NO: 30. SEQ ID NO: 19 also encodes a hydrophobic transmembrane domain which extends from about amino acid 172 to about amino acid 228 of SEQ ID NO: 24. Knowledge of these nucleic acid and amino acid sequences allows one skilled in the art to make modifications to the respective nucleic acid molecules and proteins to, for example, develop a canine $Fc_\epsilon R$ α chain protein with increased solubility and/or a truncated protein capable of detecting canine IgE, e.g., $PcFc_\epsilon R\alpha4_{197}$, spanning from about amino acid 1 to about amino acid 197 of SEQ ID NO: 20, and having SEQ ID NO: 28; or $PcFc_\epsilon R\alpha4_{173}$, spanning from about amino acid 25 to about amino acid 197 of SEQ ID NO: 20, and having SEQ ID NO: 31.

Preferred $Fc_\epsilon R$ molecules include $PcFc_\epsilon R\alpha4_{253}$, $PcFc_\epsilon R\alpha4_{229}$, $PcFc_\epsilon R\alpha4_{197}$, $PcFc_\epsilon R\alpha4_{173}$ and allelic variants thereof, as well as $PcFc_\epsilon R\alpha1_{197}$, $PcFc_\epsilon R\alpha2_{197}$, $PcFc_\epsilon R\alpha3_{199}$ (which are disclosed in the Examples section) and allelic variants thereof. Preferred nucleic acid molecules to encode a $Fc_\epsilon R$ molecules include $ncFc_\epsilon R\alpha4_{191}$, $ncFc_\epsilon R\alpha4_{687}$, $ncFc_\epsilon R\alpha4_{991}$, $ncFc_\epsilon R\alpha4_{759}$ and allelic variants thereof, as well as $ncFc_\epsilon R\alpha1_{609}$, $ncFc_\epsilon R\alpha1_{591}$, $ncFc_\epsilon R\alpha2_{609}$, $ncFc_\epsilon R\alpha2_{591}$, $ncFc_\epsilon R\alpha3_{617}$, $ncFc_\epsilon R\alpha3_{597}$ (which are disclosed in the Examples section) and allelic variants thereof. A preferred nucleic acid sequence encoding a canine $Fc_\epsilon R$ molecule includes SEQ ID NO: 3, SEQ ID NO: 6, SEQ ID NO: 8, SEQ ID NO: 11, SEQ ID NO: 13, SEQ ID NO: 16, SEQ ID NO: 19, SEQ ID NO: 22, SEQ ID NO: 24, SEQ ID NO: 27, SEQ ID NO: 30, and/or a nucleic acid molecule comprising an allelic variant of a nucleic acid molecule comprising any of said nucleic acid sequences.

An isolated canine $Fc_\epsilon R$ molecule protein of the present invention can be produced by culturing a cell capable of expressing the protein under conditions effective to produce the protein, and recovering the protein. A preferred cell to culture is a recombinant cell that is capable of expressing the protein, the recombinant cell being produced by transforming a host cell with one or more nucleic acid molecules of the present invention. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed nucleic acid molecules of the present invention can remain extrachromosomal or can integrate into one or more sites within a chromosome of the transformed (i.e., recombinant) cell in such a manner that their ability to be expressed is retained. Suitable and preferred nucleic acid molecules with which to transform a cell are as disclosed herein for suitable and preferred $Fc_\epsilon R$ nucleic acid molecules per se. Particularly preferred nucleic acid molecules to include in recombinant cells of the present invention include $ncFc_\epsilon R\alpha1_{609}$, $ncFc_\epsilon R\alpha1_{591}$, $ncFc_\epsilon R\alpha2_{609}$, $ncFc_\epsilon R\alpha2_{591}$, $ncFc_\epsilon R\alpha3_{617}$, $ncFc_\epsilon R\alpha3_{597}$, $ncFc_\epsilon R\alpha4_{591}$, $ncFc_\epsilon R\alpha4_{687}$, $ncFc_\epsilon R\alpha4_{991}$ and/or $ncFc_\epsilon R\alpha4_{759}$.

Suitable host cells to transform include any cell that can be transformed with a nucleic acid molecule of the present invention. Host cells can be either untransformed cells or cells that are already transformed with at least one nucleic acid molecule. Host cells of the present invention either can be endogenously (i.e., naturally) capable of producing a canine $Fc_\epsilon R$ molecule protein of the present invention or can be capable of producing such proteins after being transformed with at least one nucleic acid molecule of the present invention. Host cells of the present invention can be any cell capable of producing at least one protein of the present invention, and include bacterial, fungal (including yeast), parasite (including protozoa and ectoparasite), insect, other animal and plant cells.

Preferably, a recombinant cell is transfected with a recombinant molecule of the present invention. A recombinant molecule of the present invention includes at least one of any nucleic acid molecules heretofore described operatively linked to at least one of any transcription control sequence capable of effectively regulating expression of the nucleic acid molecule(s) in the cell to be transformed, examples of which are disclosed herein. Particularly preferred recombinant molecules include $pVL$-$ncFc_\epsilon R\alpha4_{591}$, $pVL$-$ncFc_\epsilon R\alpha1_{609}$, $pVL$-$ncFc_\epsilon R\alpha2_{609}$, and $pVL$-$ncFc_\epsilon R\alpha3_{617}$. Details regarding the production of $Fc_\epsilon R$ molecule nucleic acid molecule-containing recombinant molecules are disclosed herein. Particularly preferred recombinant cells of the present invention include S. frugiperda:$pVL$-$ncFc_\epsilon R\alpha4_{591}$, Trichoplusia ni:$BV$-$ncFc_\epsilon R\alpha4_{591}$, S. frugiperda:$pVL$-$ncFc_\epsilon R\alpha1_{609}$, S. frugiperda:$pVL$-$ncFc_\epsilon R\alpha2_{609}$, S. frugiperda:$pVL$-$ncFc_\epsilon R\alpha3_{608}$, Trichoplusia ni:$BV$-$ncFc_\epsilon R\alpha1_{609}$, Trichoplusia ni:$BV$-$ncFc_\epsilon R\alpha2_{609}$, and Trichoplusia ni:$BV$-$ncFc_\epsilon R\alpha3_{617}$.

A $Fc_\epsilon R$ molecule of the present invention can include chimeric molecules comprising a portion of a $Fc_\epsilon R$ molecule that binds to an IgE and a second molecule that enables the chimeric molecule to be bound to a substrate in such a manner that the $Fc_\epsilon R$ portion binds to IgE in essentially the same manner as a $Fc_\epsilon R$ molecule that is not bound to a substrate. An example of a suitable second molecule includes a portion of an immunoglobulin molecule.

A canine $Fc_\epsilon R$ molecule of the present invention can be contained in a formulation, herein referred to as a $Fc_\epsilon R$ formulation. For example, a canine $Fc_\epsilon R$ molecule can be combined with a buffer in which the $Fc_\epsilon R$ is solubilized, and/or with a carrier. Suitable buffers and carriers are known to those skilled in the art. Examples of suitable buffers include any buffer in which a $Fc_\epsilon R$ can function to selectively bind to IgE, such as, but not limited to, phosphate buffered saline, water, saline, phosphate buffer, bicarbonate buffer, HEPES buffer (N-2-hydroxyethylpiperazine-N'-2-ethanesulfonic acid buffered saline), TES buffer (Tris-EDTA buffered saline), Tris buffer and TAE buffer (Tris-acetate-EDTA). Examples of carriers include, but are not limited to, polymeric matrices, toxoids, and serum albumins, such as bovine serum albumin. Carriers can be combined with $Fc_\epsilon R$ or conjugated (i.e., attached) to $Fc_\epsilon R$ in such a manner as to not substantially interfere with the ability of the $Fc_\epsilon R$ to selectively bind to IgE.

A canine $Fc_\epsilon R$ molecule of the present invention can be bound to the surface of a cell expressing the $Fc_\epsilon R$. A preferred $Fc_\epsilon R$-bearing cell includes a recombinant cell expressing a nucleic acid molecule encoding a canine $Fc_\epsilon R$ alpha chain of the present invention. A more preferred recombinant cell of the present invention expresses a nucleic acid molecule that encodes at least one of the following proteins: $PcFc_\epsilon R\alpha 1_{197}$, $PcFc_\epsilon R\alpha 2_{197}$, $PcFc_\epsilon R\alpha 3_{199}$, $PcFc_\epsilon R\alpha 4_{253}$, $PcFc_\epsilon R\alpha 4_{229}$, $PcFc_\epsilon R\alpha 4_{197}$ and $PcFc_\epsilon R\alpha 4_{173}$. An even more preferred recombinant cell expresses a nucleic acid including $ncFc_\epsilon R\alpha 1_{609}$, $ncFc_\epsilon R\alpha 1_{591}$, $ncFc_\epsilon R\alpha 2_{609}$, $ncFc_\epsilon R\alpha 2_{591}$, $ncFc_\epsilon R\alpha 3_{617}$, $ncFc_\epsilon R\alpha 3_{597}$, $ncFc_\epsilon R\alpha 4_{591}$, $ncFc_\epsilon R\alpha 4_{687}$, $ncFc_\epsilon R\alpha 4_{991}$ and $ncFc_\epsilon R\alpha 4_{759}$, or allelic variants thereof, with a recombinant cell expressing a nucleic acid molecule comprising a nucleic acid sequence SEQ ID NO: 3, SEQ ID NO: 8, SEQ ID NO: 13 or SEQ ID NO: 27, or a nucleic acid molecule comprising an allelic variant of a nucleic acid molecule comprising SEQ ID NO: 3, SEQ ID NO: 8, SEQ ID NO: 13 or SEQ ID NO: 27, being even more preferred.

In addition, a $Fc_\epsilon R$ formulation of the present invention can include not only a $Fc_\epsilon R$ but also one or more additional antigens or antibodies useful in detecting IgE. As used herein, an antigen refers to any molecule capable of being selectively bound by an antibody. As used herein, specific binding of a first molecule to a second molecule refers to the ability of the first molecule to preferentially bind to (e.g., have higher affinity higher avidity for) the second molecule when compared to the ability of a first molecule to bind to a third molecule. The first molecule need not necessarily be the natural ligand of the second molecule. Examples of antibodies used in the present invention include, but are not limited to, antibodies that bind selectively to the constant region of an IgE heavy chain (i.e., anti-IgE isotype antibodies) or antibodies that bind selectively to an IgE having a specific antigen specificity (i.e., anti-IgE idiotypic antibodies). Examples of antigens used in the present invention include any antigen known to induce the production of IgE. Preferred antigens include allergens and parasite antigens. Allergens of the present invention are preferably derived from fungi, trees, weeds, shrubs, grasses, wheat, corn, soybeans, rice, eggs, milk, cheese, bovines (or cattle), poultry, swine, sheep, yeast, fleas, flies, mosquitos, mites, midges, biting gnats, lice, bees, wasps, ants, true bugs or ticks. A suitable flea allergen includes an allergen derived from a flea, and in particular a flea saliva antigen. Preferred flea saliva antigens include antigens such as those disclosed in PCT Patent Publication Nos. WO 96/11271, published Apr. 18, 1996, by Frank et al., U.S. Pat. No. 5,795,862, issued Aug. 18, 1998, by Frank et al., U.S. Pat. No. 5,646, 115, issued Jul. 8, 1997, by Frank et al., U.S. Pat. No. 5,840,695, issued Nov. 24, 1998, by Frank et al. (these PCT and U.S. patent publications are incorporated herein by this reference in their entirety); and U.S. patent application Ser. No. 08/487,608 (filed Jun. 7, 1995), with flea saliva products and flea saliva proteins being particularly preferred. According to the present invention, a flea saliva protein includes a protein produced by recombinant DNA methods, as well as proteins isolated by other methods disclosed in PCT Patent Publication Nos. WO 96/11271, published Apr. 18, 1996, by Frank et al., U.S. Pat. No. 5,795,862, issued Aug. 18, 1998, by Frank et al., U.S. Pat. No. 5,646,115, issued Jul. 8, 1997, by Frank et al., U.S. Pat. No. 5,840,695, issued Nov. 24, 1998, by Frank et al. (these PCT and U.S. patent publications are incorporated herein by this reference in their entirety); and U.S. patent application Ser. No. 08/487,608 (filed Jun. 7, 1995).

Preferred general allergens include those derived from grass, Meadow Fescue, Curly Dock, plantain, Mexican Firebush, Lamb's Quarters, pigweed, ragweed, sage, elm, cocklebur, Box Elder, walnut, cottonwood, ash, birch, cedar, oak, mulberry, cockroach, Dermataphagoides, Alternaria, Aspergillus, Cladosporium, Fusarium, Helminthosporium, Mucor, Penicillium, Pullularia, Rhizopus and/or Tricophyton. More preferred general allergens include those derived from Johnson Grass, Kentucky Blue Grass, Meadow Fescue, Orchard Grass, Perennial Rye Grass, Redtop Grass, Timothy Grass, Bermuda Grass, Brome Grass, Curly Dock, English Plantain, Mexican Firebush, Lamb's Quarters, Rough Pigweed Short Ragweed, Wormwood Sage, American Elm, Common Cocklebur, Box Elder, Black Walnut, Eastern Cottonwood, Green Ash, River Birch, Red Cedar, Red Oak, Red Mulberry, Cockroach, *Dermataphagoides farinae, Alternaria alternata, Aspergillus fumigatus, Cladosporium herbarum, Fusarium vasinfectum, Helminthosporium sativum, Mucor recemosus, Penicillium notatum, Pullularia pullulans, Rhizopus nigricans* and/or Tricophyton spp. Preferred parasite antigens include, but are not limited to, helminth antigens, in particular heartworm antigens, such as Di33 (described in U.S. patent application Ser. No. 08/715, 628, filed Sep. 18, 1996, to Grieve et al.; this publication is incorporated by reference herein in its entirety). The term "derived from" refers to a natural allergen of such plants or organisms (i.e., an allergen directly isolated from such plants or organisms), as well as non-natural allergens of such plants or organisms that possess at least one epitope capable of eliciting an immune response against an allergen (e.g., produced using recombinant DNA technology or by chemical synthesis).

The present invention also includes canine $Fc_\epsilon R$ mimetopes and use thereof to detect IgE. In accordance with the present invention, a "mimetope" refers to any compound that is able to mimic the ability of a canine $Fc_\epsilon R$ molecule to bind to canine IgE. A mimetope can be a peptide that has been modified to decrease its susceptibility to degradation but that still retains IgE-binding activity. Other examples of mimetopes include, but are not limited to, carbohydrate-based compounds, lipid-based compounds, nucleic acid-based compounds, natural organic compounds, synthetically derived organic compounds, anti-idiotypic antibodies and/or catalytic antibodies, or fragments thereof. A mimetope can be obtained by, for example, screening libraries of synthetic compounds for compounds capable of binding to IgE. A mimetope can also be obtained by, for example, rational drug design. In a rational drug design procedure, the three-dimensional structure of a compound of the present invention can be analyzed by, for example, nuclear magnetic resonance (NMR) or x-ray crystallography. The three-dimensional structure can then be used to predict structures of potential mimetopes by, for example, computer modeling. The predicted mimetope structures can then be produced by, for example, chemical synthesis, recombinant DNA technology, or by isolating a mimetope from a natural source. Specific examples of $Fc_\epsilon R$ mimetopes include anti-idiotypic antibodies, oligonucleotides produced using Selex® technology, peptides identified by random screening of peptide libraries and proteins identified by phage display technology.

One embodiment of the present invention is a method to detect canine IgE which includes the steps of: (a) contacting an isolated canine $Fc_\epsilon$ receptor ($Fc_\epsilon R$) molecule with a putative canine IgE-containing composition under conditions suitable for formation of a $Fc_\epsilon R$ molecule:IgE complex; and (b) detecting levels of IgE by detecting said $Fc_\epsilon R$ molecule:IgE complex. Presence of such a $Fc_\epsilon R$ molecule:IgE complex indicates that the canine is producing IgE. The present method can further include the step of determining whether a canine IgE complexed with a canine $Fc_\epsilon R$ molecule is heat labile. Certain classes of IgE are heat labile when incubated at about 56° C. for about 4 hours. Without being bound by theory, Applicants believe that heat labile forms of IgE bind to certain allergens and non-heat labile forms of IgE bind to other types of allergens. As such, detection of heat labile IgE compared with non-heat labile IgE can be used to discriminate between allergen sensitivities. For example, Applicants believe that canine IgE antibodies that bind to certain flea allergens and heartworm allergens are heat labile while canine IgE antibodies that bind to certain plant allergens are not heat labile. Thus, the presence of non-heat labile IgE can indicate that an animal is sensitive to certain plant allergens but not to certain flea or heartworm allergens. Moreover, Applicants believe that identification of heat labile IgE and non-heat labile IgE using a canine $Fc_\epsilon R$ suggests the presence of different sub-populations of IgE that may or may not have substantially similar structures to known IgE. As such, a $Fc_\epsilon R$ molecule of the present invention may be useful for detecting molecules bound by the $Fc_\epsilon R$ molecule that are not identical to a known IgE.

As used herein, canine refers to any member of the dog family, including domestic dogs, wild dogs and zoo dogs. Examples of dogs include, but are not limited to, domestic dogs, wild dogs, foxes, wolves, jackals and coyotes.

As used herein, the term "contacting" refers to combining or mixing, in this case a putative IgE-containing composition with a canine $Fc_\epsilon R$ molecule. Formation of a complex between a canine $Fc_\epsilon R$ and a canine IgE refers to the ability of the $Fc_\epsilon R$ to selectively bind to the IgE in order to form a stable complex that can be measured (i.e., detected). As used herein, the term selectively binds to an IgE refers to the ability of a $Fc_\epsilon R$ of the present invention to preferentially bind to IgE, without being able to substantially bind to other antibody isotypes. Binding between a $Fc_\epsilon R$ and an IgE is effected under conditions suitable to form a complex; such conditions (e.g., appropriate concentrations, buffers, temperatures, reaction times) as well as methods to optimize such conditions are known to those skilled in the art, and examples are disclosed herein. Examples of complex formation conditions are also disclosed in, for example, in Sambrook et al., *Molecular Cloning: A Laboratory Manual*, Cold Spring Harbor Labs Press, 1989; the reference Sambrook et al., ibid., is incorporated by reference herein in its entirety.

As used herein, the term "detecting complex formation" refers to determining if any complex is formed, i.e., assaying for the presence (i.e., existence) of a complex. If complexes are formed, the amount of complexes formed can, but need not be, determined. Complex formation, or selective binding, between canine $Fc_\epsilon R$ and canine IgE in the composition can be measured (i.e., detected, determined) using a variety of methods standard in the art (see, for example, Sambrook et al. ibid.), examples of which are disclosed herein.

In one embodiment, a putative canine IgE-containing composition of the present method includes a biological sample from a canine. A suitable biological sample includes, but is not limited to, a bodily fluid composition or a cellular composition. A bodily fluid refers to any fluid that can be collected (i.e., obtained) from an animal, examples of which include, but are not limited to, blood, serum, plasma, urine, tears, aqueous humor, central nervous system fluid (CNF), saliva, lymph, nasal secretions, milk and feces. Such a composition of the present method can, but need not be, pretreated to remove at least some of the non-IgE isotypes of immunoglobulin and/or other proteins, such as albumin, present in the fluid. Such removal can include, but is not limited to, contacting the bodily fluid with a material, such as Protein G, to remove IgG antibodies and/or affinity purifying IgE antibodies from other components of the body fluid by exposing the fluid to, for example, Concanavalin A. In another embodiment, a composition includes collected bodily fluid that is pretreated to concentrate immunoglobulin contained in the fluid. For example, immunoglobulin contained in a bodily fluid can be precipitated from other proteins using ammonium sulfate. A preferred composition of the present method is serum.

In another embodiment, a composition of the present method includes an IgE-producing cell. Such a cell can have IgE bound to the surface of the cell and/or can secrete IgE. Examples of such cells include basophil cells and myeloma cells. IgE can be bound to the surface of a cell, for example by being either bound directly to the membrane of a cells or bound to a molecule (e.g., an antigen) bound to the surface of the cell.

A complex can be detected in a variety of ways including, but not limited to, use of one or more of the following assays: an enzyme-linked immunoassay, a radioimmunoassay, a fluorescence immunoassay, a chemiluminescent assay, a lateral flow assay, an agglutination assay, a particulate-based assay (e.g., using particulates such as, but not limited to, magnetic particles or plastic polymers, such as latex or polystyrene beads), an immunoprecipitation assay, a BioCore™ assay (e.g., using colloidal gold) and an immunoblotting assay (e.g., a western blot). Such assays are well known to those skilled in the art. Assays can be used to give qualitative or quantitative results depending on how they are used. Some assays, such as agglutination, particulate separation, and immunoprecipitation, can be observed visually (e.g., either by eye or by a machine, such as a densitometer or spectrophotometer) without the need for a detectable marker. In other assays, conjugation (i.e., attachment) of a detectable marker to the $Fc_\epsilon R$ or to a reagent that selectively binds to the $Fc_\epsilon R$ or to the IgE being detected (described in more detail below) aids in detecting complex formation. Examples of detectable markers include, but are not limited to, a radioactive label, a fluorescent label, a chemiluminescent label, a chromophoric label or a ligand. A ligand refers to a molecule that binds selectively to another molecule. Preferred detectable markers include, but are not limited to, fluorescein, a radioisotope, a phosphatase (e.g., alkaline phosphatase), biotin, avidin, a peroxidase (e.g., horseradish peroxidase) and biotin-related compounds or avidin-related compounds (e.g., streptavidin or ImmunoPure® NeutrAvidin®). Preferably, biotin is conjugated to an alpha chain of a $Fc_\epsilon R$. Preferably a carbohydrate group of the $Fc_\epsilon R$ alpha chain is conjugated to biotin.

In one embodiment, a complex is detected by contacting a putative IgE-containing composition with a canine $Fc_\epsilon R$ molecule that is conjugated to a detectable marker. A suitable detectable marker to conjugate to a $Fc_\epsilon R$ molecule includes, but is not limited to, a radioactive label, a fluorescent label, a chemiluminescent label or a chromophoric label. A detectable marker is conjugated to a $Fc_\epsilon R$ molecule or a reagent in such a manner as not to block the ability of the $Fc_\epsilon R$ or reagent to bind to the IgE being detected. Preferably, a carbohydrate group of a $Fc_\epsilon R$ is conjugated to biotin.

In another embodiment, a $Fc_\epsilon R$ molecule:IgE complex is detected by contacting a putative IgE-containing composition with a $Fc_\epsilon R$ molecule and then contacting the complex with an indicator molecule. Suitable indicator molecules of the present invention include molecules that can bind to either the $Fc_\epsilon R$ molecule or to the IgE antibody. As such, an indicator molecule can comprise, for example, a $Fc_\epsilon R$ molecule, an antigen, an antibody and a lectin, depending upon which portion of the $Fc_\epsilon R$ molecule:IgE complex is being detected. Preferred identifying labeled compounds that are antibodies include, for example, anti-IgE antibodies and anti-$Fc_\epsilon R$ antibodies. Preferred lectins include those lectins that bind to high-mannose groups. More preferred lectins bind to high-mannose groups present on a $Fc_\epsilon R$ molecule of the present invention produced in insect cells. An indicator molecule itself can be attached to a detectable marker of the present invention. For example, an antibody can be conjugated to biotin, horseradish peroxidase, alkaline phosphatase or fluorescein.

In one preferred embodiment, a $Fc_\epsilon R$ molecule:IgE complex is detected by contacting the complex with a reagent that selectively binds to a $Fc_\epsilon R$ molecule of the present invention. Examples of such a reagent include, but are not limited to, an antibody that selectively binds to a $Fc_\epsilon R$ molecule (referred to herein as an anti-$Fc_\epsilon R$ antibody) or a compound that selectively binds to a detectable marker conjugated to a $Fc_\epsilon R$ molecule. $Fc_\epsilon R$ molecules conjugated to biotin are preferably detected using streptavidin, more preferably using ImmunoPure® NeutrAvidin® (available from Pierce, Rockford, Ill.).

In another preferred embodiment, a $Fc_\epsilon R$ molecule:IgE complex is detected by contacting the complex with a reagent that selectively binds to an IgE antibody (referred to herein as an anti-IgE reagent). Examples of such an anti-IgE reagent include, but are not limited to, a secondary antibody that is an anti-isotype antibody (e.g., an antibody that selectively binds to the constant region of an IgE), an antibody-binding bacterial surface protein (e.g., Protein A or Protein G), an antibody-binding cell (e.g., a B cell, a T cell, a natural killer cell, a polymorphonuclear leukocyte cell, a monocyte cell or a macrophage cell), an antibody-binding eukaryotic cell surface protein (e.g., an Fc receptor), and an antibody-binding complement protein. Preferred anti-IgE reagents include, but are not limited to, D9 (provided by Doug DeBoer, University of Wisconsin), and CMI antibody #9, CMI antibody #19, CMI antibody #59 and CMI antibody #71 (available from Custom Monoclonal International, West Sacramento, Calif.). In particular, as used herein, an anti-IgE antibody includes not only a complete antibody but also any subunit or portion thereof that is capable of selectively binding to an IgE heavy chain constant region. For example, a portion of an anti-IgE reagent can include an Fab fragment or a F(ab')$_2$ fragment, which are described in detail in Janeway et al., in *Immunobiology, the Immune System in Health and Disease,* Garland Publishing, Inc., NY, 1996 (which is incorporated herein by this reference in its entirety).

In one embodiment a complex can be formed and detected in solution. In another embodiment, a complex can be formed in which one or more members of the complex are immobilized on (e.g., coated onto) a substrate. Immobilization techniques are known to those skilled in the art. Suitable substrate materials include, but are not limited to, plastic, glass, gel, celluloid, paper, PVDF (poly-vinylidene-fluoride), nylon, nitrocellulose, and particulate materials such as latex, polystyrene, nylon, nitrocellulose, agarose and magnetic resin. Suitable shapes for substrate material include, but are not limited to, a well (e.g., microtiter dish well), a plate, a dipstick, a bead, a lateral flow apparatus, a membrane, a filter, a tube, a dish, a celluloid-type matrix, a magnetic particle, and other particulates. A particularly preferred substrate comprises an ELISA plate, a dipstick, a radioimmunoassay plate, agarose beads, plastic beads, latex beads, immunoblot membranes and immunoblot papers. In one embodiment, a substrate, such as a particulate, can include a detectable marker.

A preferred method to detect canine IgE is an immunosorbent assay. An immunoabsorbent assay of the present invention comprises a capture molecule and an indicator molecule. A capture molecule of the present invention binds to an IgE in such a manner that the IgE is immobilized to a substrate. As such, a capture molecule is preferably immobilized to a substrate of the present invention prior to exposure of the capture molecule to a putative IgE-containing composition. An indicator molecule of the present invention detects the presence of an IgE bound to a capture molecule. As such, an indicator molecule preferably is not immobilized to the same substrate as a capture molecule prior to exposure of the capture molecule to a putative IgE-containing composition.

A preferred immunoabsorbent assay method includes a step of either: (a) binding a canine $Fc_\epsilon R$ molecule to a substrate prior to contacting a canine $Fc_\epsilon R$ molecule with a putative IgE-containing composition to form a canine $Fc_\epsilon R$ molecule-coated substrate; or (b) binding a putative canine IgE-containing composition to a substrate prior to contacting a canine $Fc_\epsilon R$ molecule with a putative IgE-containing composition to form a putative IgE-containing composition-coated substrate. Preferably, the substrate is a non-coated substrate, an antigen-coated substrate or an anti-IgE antibody-coated substrate.

Both a capture molecule and an indicator molecule of the present invention are capable of binding to an IgE. Preferably, a capture molecule binds to a different region of an IgE than an indicator molecule, thereby allowing a capture molecule to be bound to an IgE at the same time as an indicator molecule. The use of a reagent as a capture molecule or an indicator molecule depends upon whether the molecule is immobilized to a substrate when the molecule is exposed to an IgE. For example, a canine $Fc_\epsilon R$ molecule of the present invention is used as a capture molecule when the $Fc_\epsilon R$ molecule is bound to a substrate. Alternatively, a canine $Fc_\epsilon R$ molecule is used as an indicator molecule when the $Fc_\epsilon R$ molecule is not bound to a substrate. Suitable molecules for use as capture molecules or indicator molecules include, but are not limited to, a canine $Fc_\epsilon R$ molecule of the present invention, an antigen reagent or an anti-IgE antibody reagent of the present invention.

An immunoabsorbent assay of the present invention can further comprise one or more layers and/or types of secondary molecules or other binding molecules capable of detecting the presence of an indicator molecule. For example, an untagged (i.e., not conjugated to a detectable marker) secondary antibody that selectively binds to an indicator molecule can be bound to a tagged (i.e., conjugated to a detectable marker) tertiary antibody that selectively binds to the secondary antibody. Suitable secondary antibodies, tertiary antibodies and other secondary or tertiary molecules can be selected by those of skill in the art. Preferred secondary molecules of the present invention include an antigen, an anti-IgE idiotypic antibody and an anti-IgE isotypic antibody. Preferred tertiary molecules can be selected by a skilled artisan based upon the characteristics of the secondary molecule. The same strategy is applied for subsequent layers.

In one embodiment, a desired antigen is used as a capture molecule by being immobilized on a substrate, such as a microtiter dish well or a dipstick. Preferred antigens include those disclosed herein. A biological sample collected from an animal is applied to the substrate and incubated under conditions suitable (i.e., sufficient) to allow for antigen:IgE complex formation bound to the substrate (i.e., IgE in a sample binds to an antigen immobilized on a substrate). Excess non-bound material (i.e., material from the biological sample that has not bound to the antigen), if any, is removed from the substrate under conditions that retain antigen:IgE complex binding to the substrate. Preferred conditions are described generally in Sambrook et al., ibid. An indicator molecule that can selectively bind to an IgE bound to the antigen is added to the substrate and incubated to allow formation of a complex between the indicator molecule and the antigen:IgE complex. The indicator molecule can be conjugated to a detectable marker (preferably to an enzyme label, to a colorimetric label, to a fluorescent label, to a radioisotope, or to a ligand such as of the biotin or avidin family). Excess indicator molecule is removed, a developing agent is added if required, and the substrate is submitted to a detection device for analysis. A preferred indicator molecule for this embodiment is a canine $Fc_\epsilon R$ molecule, preferably conjugated to biotin, to a fluorescent label or to an enzyme label.

In one embodiment, a canine $Fc_\epsilon R$ molecule is used as a capture molecule by being immobilized on a substrate, such as a microtiter dish well or a dipstick. A biological sample collected from an animal is applied to the substrate and incubated under conditions suitable to allow for $Fc_\epsilon R$ molecule:IgE complex formation bound to the substrate. Excess non-bound material, if any, is removed from the substrate under conditions that retain $Fc_\epsilon R$ molecule:IgE complex binding to the substrate. An indicator molecule that can selectively bind to an IgE bound to the $Fc_\epsilon R$ is added to the substrate and incubated to allow formation of a complex between the indicator molecule and the $Fc_\epsilon R$ molecule:IgE complex. Preferably, the indicator molecule is conjugated to a detectable marker, preferably to an enzyme label, to a colorimetric label, to a fluorescent label, to a radioisotope, or to a ligand such as of the biotin or avidin family. Excess indicator molecule is removed, a developing agent is added if required, and the substrate is submitted to a detection device for analysis. A preferred indicator molecule for this embodiment is an antigen that will bind to IgE in the biological sample or an anti-IgE isotype or idiotype antibody, either preferably being conjugated to fluorescein, an enzyme or biotin.

In one embodiment, an anti-IgE antibody (e.g., isotype- or idiotype-specific antibody) is used as a capture molecule by being immobilized on a substrate, such as a microtiter dish well or a dipstick. A biological sample collected from a canine is applied to the substrate and incubated under conditions suitable to allow for anti-IgE antibody:IgE complex formation bound to the substrate. Excess non-bound material, if any, is removed from the substrate under conditions that retain anti-IgE antibody:IgE complex binding to the substrate. A canine $Fc_\epsilon R$ molecule is added to the substrate and incubated to allow formation of a complex between the canine $Fc_\epsilon R$ molecule and the anti-IgE antibody:IgE complex. Preferably, the canine $Fc_\epsilon R$ molecule is conjugated to a detectable marker (preferably to biotin, an enzyme label or a fluorescent label). Excess $Fc_\epsilon R$ molecule is removed, a developing agent is added if required, and the substrate is submitted to a detection device for analysis.

In one embodiment, an immunosorbent assay of the present invention does not utilize a capture molecule. In this embodiment, a biological sample collected from a canine is applied to a substrate, such as a microtiter dish well or a dipstick, and incubated under conditions suitable to allow for IgE binding to the substrate. Any IgE present in the bodily fluid is immobilized on the substrate. Excess non-bound material, if any, is removed from the substrate under conditions that retain IgE binding to the substrate. A canine $Fc_\epsilon R$ molecule is added to the substrate and incubated to allow formation of a complex between the canine $Fc_\epsilon R$ molecule and canine IgE. Preferably, the $Fc_\epsilon R$ molecule is conjugated to a detectable marker (preferably to biotin, an enzyme label or a fluorescent label). Excess $Fc_\epsilon R$ molecule is removed, a developing agent is added if required, and the substrate is submitted to a detection device for analysis.

Another preferred method to detect canine IgE is a lateral flow assay, examples of which are disclosed in U.S. Pat. No. 5,424,193, issued Jun. 13, 1995, by Pronovost et al.; U.S. Pat. No. 5,415,994, issued May 16, 1995, by Imrich et al; WO 94/29696, published Dec. 22, 1994, by Miller et al.; and WO 94/01775, published Jan. 20, 1994, by Pawlak et al.; each of these patent publications is incorporated by reference herein in its entirety. In one embodiment, a biological sample is placed in a lateral flow apparatus that includes the following components: (a) a support structure defining a flow path; (b) a labeling reagent comprising a bead conjugated to an antigen, the labeling reagent being impregnated within the support structure in a labeling zone; and (c) a capture reagent comprising a canine IgE-binding composition. Preferred antigens include those disclosed herein. The capture reagent is located downstream of the labeling reagent within a capture zone fluidly connected to the labeling zone in such a manner that the labeling reagent can flow from the labeling zone into the capture zone. The support structure comprises a material that does not impede the flow of the beads from the labeling zone to the capture zone. Suitable materials for use as a support structure include ionic (i.e., anionic or cationic) material. Examples of such a material include, but are not limited to, nitrocellulose (NC), PVDF and carboxymethylcellulose (CM). The support structure defines a flow path that is lateral and is divided into zones, namely a labeling zone and a capture zone. The apparatus can further comprise a sample receiving zone located along the flow path, more preferably upstream of the labeling reagent. The flow path in the support structure is created by contacting a portion of the support structure downstream of the capture zone, preferably at the end of the flow path, to an absorbent capable of absorbing excess liquid from the labeling and capture zones.

In this embodiment, the biological sample is applied to the sample receiving zone which includes a portion of the support structure. The labeling zone receives the sample from the sample receiving zone which is directed downstream by the flow path. The labeling zone comprises the labeling reagent that binds to IgE. A preferred labeling reagent is an antigen conjugated, either directly or through a linker, to a plastic bead substrate, such as to a latex bead. The substrate also includes a detectable marker, preferably a colorimetric marker. Typically, the labeling reagent is impregnated to the support structure by drying or lyophilization. The sample structure also comprises a capture zone downstream of the labeling zone. The capture zone receives labeling reagent from the labeling zone which is directed downstream by the flow path. The capture zone contains the capture reagent, preferably a canine $Fc_\epsilon R$ molecule of the present invention that immobilizes canine IgE complexed to the antigen in the capture zone. The capture reagent is preferably fixed to the support structure by drying or lyophilization. The labeling reagent accumulates in the capture zone and the accumulation is assessed visually or by an optical detection device.

In another embodiment, a lateral flow apparatus used to detect canine IgE includes: (a) a support structure defining a flow path; (b) a labeling reagent comprising a canine $Fc_\epsilon R$ molecule of the present invention, the labeling reagent impregnated within the support structure in a labeling zone; and (c) a capture reagent comprising an antigen, the capture reagent being located downstream of the labeling reagent within a capture zone fluidly connected to the labeling zone in such a manner that the labeling reagent can flow from the labeling zone into the capture zone. The apparatus preferably also includes a sample receiving zone located along the flow path, preferably upstream of the labeling reagent. The apparatus preferably also includes an absorbent located at the end of the flow path.

One embodiment of the present invention is an inhibition assay in which the presence of canine IgE in a putative canine IgE-containing composition is determined by adding such composition to a canine $Fc_\epsilon R$ molecule of the present invention and an isolated canine IgE known to bind to the $Fc_\epsilon R$ molecule. The absence of binding of the $Fc_\epsilon R$ molecule to the known IgE indicating the presence of IgE in the putative IgE-containing composition.

The present invention also includes kits to detect canine IgE based, for example, on the disclosed detection methods. One embodiment is a kit to detect canine IgE comprising a canine $Fc_\epsilon$ receptor ($Fc_\epsilon R$) molecule and a means for detecting a canine IgE. Suitable and preferred canine $Fc_\epsilon R$ molecules are disclosed herein. Suitable means of detection include compounds disclosed herein that bind to either the canine $Fc_\epsilon R$ molecule or to a canine IgE. A preferred kit of the present invention further comprises a detection means including one or more antigens such as those disclosed herein, an antibody capable of selectively binding to canine IgE such as those disclosed herein and/or a compound capable of binding to a detectable marker conjugated to a canine $Fc_\epsilon R$ molecule (e.g., avidin, streptavidin and ImmunoPure® NeutrAvidin when the detectable marker is biotin).

A preferred embodiment of a kit of the present invention is a flea allergen kit comprising a flea allergen such as those disclosed herein. A particularly preferred flea allergen for use with a flea allergen kit includes a flea saliva product or a flea saliva protein.

Another preferred kit of the present invention is a general allergen kit comprising an allergen common to all regions of the United States and a canine $Fc_\epsilon R$ molecule of the present invention. As used herein, a "general allergen" kit refers to a kit comprising allergens that are found substantially throughout the United States (i.e., essentially not limited to certain regions of the United States). A general allergen kit provides an advantage over regional allergen kits because a single kit can be used to test a canid from any geographical location in the United States. Suitable and preferred general allergens for use with a general allergen kit of the present invention include those general allergens disclosed herein.

Another preferred kit of the present invention is a food allergen kit comprising (a) a food allergen such as beef, chicken, pork, a mixture of fish, such as cod, halibut or and tuna, egg, milk, Brewer's yeast, whole wheat, corn, soybean, cheese and/or rice, and (b) a canine $Fc_\epsilon R$ molecule of the present invention. Preferably, the beef, chicken, pork, fish, corn and rice, are cooked.

A preferred kit of the present invention is one in which the allergen is immobilized to a substrate. If a kit comprises two or more antigens, the kit can comprise one or more compositions, each composition comprising one antigen. As such, each antigen can be tested separately. A kit can also contain two or more diagnostic reagents for detecting canine IgE, additional isolated canine IgE antigens and/or antibodies as disclosed herein. Particularly preferred are kits used in a lateral flow assay format. It is within the scope of the present invention that a lateral flow assay kit can include one or more lateral flow assay apparatuses. Multiple lateral flow apparatuses can be attached to each other at one end of each apparatus, thereby creating a fan-like structure.

In particular, a method and kit of the present invention are useful for diagnosing abnormal conditions in animals that are associated with changing levels of canine IgE. Particularly preferred conditions to diagnose include allergies, parasitic infections and neoplasia. For example, a method and kit of the present invention are particularly useful for detecting flea allergy dermatitis (FAD), when such method or kit includes the use of a flea saliva antigen. FAD is defined as a hypersensitive response to fleabites. Preferably, a putative IgE-containing composition is obtained from an animal suspected of having FAD. In addition, methods and kits of the present invention are particularly useful for detecting helminth infection, in particular heartworm infection, when such methods or kits include the use of a helminth antigen, such as Di33. Preferably, a putative canine IgE-containing composition is obtained from a canine suspected of having a helminth infection.

The following examples are provided for the purposes of illustration and are not intended to limit the scope of the present invention.

EXAMPLES

It is to be noted that the Examples include a number of molecular biology, microbiology, immunology and biochemistry techniques considered to be known to those skilled in the art. Disclosure of such techniques can be found, for example, in Sambrook et al., ibid., and related references.

Example 1

This example describes the construction of recombinant baculoviruses expressing a truncated portion of the α chain of canine $Fc_\epsilon$ receptor.

Recombinant molecules pVL-ncFc$_\epsilon$R$\alpha$1$_{609}$, pVL-ncFc$_\epsilon$R$\alpha$2$_{609}$, and pVL-ncFc$_\epsilon$R$\alpha$3$_{617}$, each containing nucleic acid molecules encoding the extracellular domain of the canine Fc$_\epsilon$R $\alpha$ chain, operatively linked to baculovirus polyhedron transcription control sequences were produced in the following manner. Three different canine Fc$_\epsilon$R $\alpha$ chain extracellular domain nucleic acid molecule-containing fragments, each of about 608 to about 609 nucleotides were amplified by polymerase chain reaction (PCR) from either a canine splenic mononuclear cell cDNA library or a canine lymph node mononuclear cell cDNA library, each library produced using standard techniques, using a forward primer CIERMet containing a BamHI site, having the nucleic acid sequence 5'-TGC GGA TCC AAT ATG CCT GCT TCC ATG GGA G-3' (denoted SEQ ID NO: 1) and a reverse primer CIERSec containing an EcoRI site, having the nucleic acid sequence 5'-TTG GAA TTC TTA CTC TTT TTT CAC AAT AAT GTT G-3' (denoted herein as SEQ ID NO: 2). The resulting PCR products were digested with BamHI and EcoRI to produce the following nucleic acid molecules: ncFc$_\epsilon$R$\alpha$1$_{609}$ (also denoted ncFc$_\epsilon$R$\alpha$LN4$_{609}$), ncFc$_\epsilon$R$\alpha$2$_{609}$ (also denoted ncFc$_\epsilon$R$\alpha$SPL6$_{609}$) and ncFc$_\epsilon$R$\alpha$3$_{617}$ (also denoted ncFc$_\epsilon$R$\alpha$SPL3R$_{617}$). Nucleic acid molecule ncFc$_\epsilon$R$\alpha$1$_{609}$ was obtained from the PCR reaction derived from the canine lymph node mononuclear cell cDNA library. Nucleic acid molecules ncFc$_\epsilon$R$\alpha$2$_{609}$ and ncFc$_\epsilon$R$\alpha$3$_{617}$ were obtained from the PCR reaction derived from the canine splenic mononuclear cell cDNA library. Nucleic acid molecules ncFc$_\epsilon$R$\alpha$1$_{609}$, ncFc$_\epsilon$R$\alpha$2$_{609}$, and ncFc$_\epsilon$R$\alpha$3$_{617}$ each were sequenced by the Sanger dideoxy chain termination method, using the PRISM™ Ready Dye Terminator Cycle Sequencing Kit with Ampli Taq DNA Polymerase, FS (available from the Perkin-Elmer Corporation, Norwalk, Conn.). Nucleic acid molecules ncFc$_\epsilon$R$\alpha$1$_{609}$, ncFc$_\epsilon$R$\alpha$2$_{609}$, and ncFc$_\epsilon$R$\alpha$3$_{617}$ each contained an about 608 to an about 609 nucleotide fragment encoding the extracellular domain of the canine Fc$_\epsilon$R $\alpha$ chain, the coding strands of which have nucleic acid sequences denoted SEQ ID NO: 3, SEQ ID NO: 8, and SEQ ID NO: 13, respectively. The complement of SEQ ID NO: 3 is represented herein by SEQ ID NO: 5. The complement of SEQ ID NO: 8 is represented herein by SEQ ID NO: 10. The complement of SEQ ID NO: 13 is represented herein by SEQ ID NO: 15.

Translation of SEQ ID NO: 3 indicates that nucleic acid molecule ncFc$_\epsilon$R$\alpha$1$_{609}$ encodes a Fc$_\epsilon$R protein of about 197 amino acids, referred to herein as PcFc$_\epsilon$R$\alpha$1$_{197}$, having amino acid sequence SEQ ID NO: 4, assuming an open reading frame having a start codon spanning from about nucleotide 10 through about nucleotide 12 of SEQ ID NO: 3 and a stop codon spanning from about nucleotide 601 through about nucleotide 603 of SEQ ID NO: 3. This open reading frame, excluding the stop codon, comprises nucleic acid molecule ncFc$_\epsilon$R$\alpha$1$_{191}$ of the present invention, the nucleic acid sequence of which is represented herein by SEQ ID NO: 6. The complement of SEQ ID NO: 6 is represented herein by SEQ ID NO: 7.

Translation of SEQ ID NO: 8 indicates that nucleic acid molecule ncFc$_\epsilon$R$\alpha$2$_{609}$ encodes a Fc$_\epsilon$R protein of about 197 amino acids, referred to herein as PcFc$_\epsilon$R$\alpha$2$_{197}$, having amino acid sequence SEQ ID NO: 9, assuming an open reading frame having a start codon spanning from about nucleotide 10 through about nucleotide 12 of SEQ ID NO: 8 and a stop codon spanning from about nucleotide 601 through about nucleotide 603 of SEQ ID NO: 8. This open reading frame, excluding the stop codon, comprises nucleic acid molecule ncFc$_\epsilon$R$\alpha$2$_{591}$ of the present invention, the nucleic acid sequence of which is represented herein by SEQ ID NO: 11. The complement of SEQ ID NO: 11 is represented herein by SEQ ID NO: 12.

Translation of SEQ ID NO: 13 indicates that nucleic acid molecule ncFc$_\epsilon$R$\alpha$3$_{617}$ encodes a Fc$_\epsilon$R protein of about 199 amino acids, referred to herein as PcFc$_\epsilon$R$\alpha$3$_{199}$, having amino acid sequence SEQ ID NO: 14, assuming that the initiation codon spans from about nucleotide 10 through about nucleotide 12 of SEQ ID NO: 13 and the last codon spans from about nucleotide 595 through about nucleotide 597 of SEQ ID NO: 13. This open reading frame comprises nucleic acid molecule ncFc$_\epsilon$R$\alpha$3$_{597}$ of the present invention, the nucleic acid sequence of which is represented herein by SEQ ID NO: 16. The complement of SEQ ID NO: 16 is represented herein by SEQ ID NO: 17.

In order to produce baculovirus recombinant molecules capable of directing the production of PcFc$_\epsilon$RE1$_{197}$, PcFc$_\epsilon$R$\alpha$2$_{197}$, and PcFc$_\epsilon$R$\alpha$3$_{199}$, nucleic acid molecules ncFc$_\epsilon$R$\alpha$1$_{609}$, ncFc$_\epsilon$R$\alpha$2$_{609}$, and ncFc$_\epsilon$R$\alpha$3$_{617}$ were subcloned into unique BamHI and EcoRI sites of pVL1393 baculovirus shuttle plasmid (available from Pharmingen, San Diego, Calif.) to produce recombinant molecules referred to herein as pVL-ncFc$_\epsilon$R$\alpha$1$_{609}$, pVL-ncFc$_\epsilon$R$\alpha$2$_{609}$, and pVL-ncFc$_\epsilon$R$\alpha$3$_{617}$, respectively. The resultant recombinant molecules pVL-ncFc$_\epsilon$R$\alpha$1$_{609}$, pVL-ncFc$_\epsilon$R$\alpha$2$_{609}$, and pVL-ncFc$_\epsilon$R$\alpha$3$_{617}$ were verified for proper insert orientation by restriction mapping.

Recombinant molecules pVL-ncFc$_\epsilon$R$\alpha$1$_{609}$, pVL-ncFc$_\epsilon$R$\alpha$2$_{609}$, and pVL-ncFc$_\epsilon$R$\alpha$3$_{617}$ were co-transfected with a linear Baculogold™ baculovirus DNA (available from Pharmingen) into S. frugiperda Sf9 cells (available from Invitrogen Corp., San Diego, Calif.) using methods prescribed by the manufacturer to form recombinant cells S. frugiperda:pVL-ncFc$_\epsilon$R$\alpha$1$_{609}$, S. frugiperda:pVL-ncFc$_\epsilon$R$\alpha$2$_{609}$, and S. frugiperda:pVL-ncFc$_\epsilon$R$\alpha$3$_{617}$. Recombinant baculoviruses were plaque purified and amplified from each transfection by methods well known to those skilled in the art, to produce recombinant baculoviruses BV-ncFc$_\epsilon$R$\alpha$1$_{609}$, BV-ncFc$_\epsilon$R$\alpha$2$_{609}$, and BV-ncFc$_\epsilon$R$\alpha$3$_{617}$, respectively.

Example 2

This example describes the production of PcFc$_\epsilon$R$\alpha$1$_{197}$, PcFc$_\epsilon$R$\alpha$2$_{197}$, and PcFc$_\epsilon$R$\alpha$3$_{199}$ canine Fc$_\epsilon$R $\alpha$ chain proteins.

About 1.5 liter cultures of serum-free ex-Cell Medium (available from Invitrogen) were seeded with about 1×10$^6$ Trichoplusia ni cells (High Five™ cells; available from Invitrogen) per milliliters (ml) of medium. The cell cultures were inoculated with recombinant baculoviruses BV-ncFc$_\epsilon$R$\alpha$1$_{609}$, BV-ncFc$_\epsilon$R$\alpha$2$_{609}$, and BV-ncFc$_\epsilon$R$\alpha$3$_{617}$, respectively, at multiplicities of infection (MOI) of about 2 to about 5 plaque forming units (pfu) per cell to produce recombinant cells Trichoplusia ni-BV-ncFc$_\epsilon$R$\alpha$1$_{609}$, Trichoplusia ni-BV-ncFc$_\epsilon$R$\alpha$2$_{609}$, and Trichoplusia ni-BV-ncFc$_\epsilon$R$\alpha$3$_{617}$. The infections were allowed to proceed at a controlled temperature of 27° C. for 48 hours, to produce recombinant proteins of PcFc$_\epsilon$R$\alpha$1$_{197}$, PcFc$\epsilon$R$\alpha$2$_{197}$, and PcFc$_\epsilon$R$\alpha$3$_{199}$. Following infection, cells were separated from the medium by centrifugation, and the medium was frozen at −70° C.

Example 3

This example describes the binding of PcFc$_\epsilon$R$\alpha$1$_{197}$, PcFc$_\epsilon$R$\alpha$2$_{197}$, or PcFc$_\epsilon$R$\alpha$3$_{199}$ protein to canine IgE.

About 4.5 ml of the culture media described immediately above containing PcFc$_\epsilon$R$\alpha$1$_{197}$, PcFc$_\epsilon$R$\alpha$2$_{197}$, or PcFc$_\epsilon$R$\alpha$3$_{199}$, respectively, were loaded onto columns comprising a canine IgE monoclonal antibody (a gift from Chris Grant, Custom Monoclonals International, West Sacramento, Calif.) linked to SEPHAROSE 4B™ beads. Each column was washed with about 4 ml of carbonate buffer (0.1 M NaHCO$_3$, pH 8.3 and 0.5 M NaCl). Protein bound to the IgE on each column was eluted from the column using about 3 ml of 0.1 M glycine-HCl, pH 2.8. Each column was further washed with about 1 ml of carbonate buffer and then with about 4 ml of buffer comprising 0.1 M NaHCO$_3$, pH 8.3. The elution samples and wash samples from a given column were combined and concentrated to a volume of about 0.35 ml. The eluted protein from each column was resolved on separate 14% Tris-glycine polyacrylamide-SDS gels. The gels were then stained with coomassie stain. A diffused band was observed at about 31 kilodaltons (kD).

Amino (N-) terminal amino acid sequencing analysis was performed on protein contained in the diffused band using standard procedures known to those in the art (see, for example, Geisow et al., 1989, in *Protein Sequencing: A Practical Approach*, J B C Findlay and M J Geisow (eds.), IRL Press, Oxford, England, pp. 85–98; Hewick et al., 1981, J. Biol. Chem., Vol. 256, pp. 7990–7997). The N-terminal partial amino acid sequence of a protein contained in the band was determined to be S D T L K P T V X M N P P X N L I (as represented in standard single letter code, and denoted herein as SEQ ID NO: 18; "X" represents any amino acid). Comparison of SEQ ID NO: 18 and the amino acid sequence of the canine Fc$_\epsilon$R alpha chain reported in Hayashi et al., ibid., indicated that PcFc$_\epsilon$R$\alpha$1$_{197}$, PcFc$_\epsilon$R$\alpha$2$_{197}$, and PcFc$_\epsilon$R$\alpha$3$_{199}$, expressed in baculovirus, each bound to canine IgE antibodies.

Example 4

This example describes the isolation, by DNA hybridization, and sequencing of a nucleic acid molecule encoding the Fc$_\epsilon$R $\alpha$ chain from *Canis canis*.

A. Isolation of nucleic acid molecule ncFc$_\epsilon$R$\alpha$4$_{991}$

A nucleic acid molecule was isolated from a canine mast cell cDNA library by the molecule's ability to hybridize with a $^{32}$P-labeled probe derived from a PCR clone encoding the canine Fc$_\epsilon$R $\alpha$ chain. The canine mast cell cDNA library was prepared using standard techniques. Using a modification of the protocol described in the cDNA Synthesis Kit, the mast cell cDNA library was screened, using duplicate plaque lifts, with a $^{32}$P-labeled probe comprising ncFc$_\epsilon$R$\alpha$1$_{609}$ (SEQ ID NO: 3). A plaque purified clone containing a canine nucleic acid molecule encoding the Fc$_\epsilon$R $\alpha$ chain was converted into a double stranded recombinant molecule, using the ExAssist™ helper phage and SOLR™ *E. coli* according to the in vivo excision protocol described in the ZAP-cDNA Synthesis Kit (available from Stratagene). Double-stranded plasmid DNA was prepared using an alkaline lysis protocol, such as that described in Sambrook et al., ibid. The plasmid comprised a canine Fc$_\epsilon$R $\alpha$ chain nucleic acid molecule of about 991 nucleotides denoted herein as ncFc$_\epsilon$R$\alpha$4$_{991}$.

B. Sequence analysis of nucleic acid molecule ncFc$_\epsilon$R$\alpha$4$_{991}$

The nucleic acid molecule ncFc$_\epsilon$R$\alpha$4$_{991}$ was sequenced by standard Sanger dideoxy chain termination sequencing techniques (see, for example, Sambrook et al, ibid.). DNA sequence analysis, including the compilation of sequences and the determination of open reading frames, were performed using the MacVector™ program (available from the Eastman Kodak Company, New Haven, Conn.), or the DNAsis™ program (available from Hitachi Software, San Bruno, Calif.). Protein sequence analysis, including the determination of molecular weight and isoelectric point (pI) was performed using the MacVector™ program.

The nucleic acid sequence of the coding strand of ncFc$_\epsilon$R$\alpha$4$_{991}$ is denoted herein as SEQ ID NO: 19. Translation of SEQ ID NO: 19 suggests that nucleic acid molecule ncFc$_\epsilon$R$\alpha$4$_{991}$ encodes a full-length canine Fc$_\epsilon$R $\alpha$ chain protein of about 253 amino acids, referred to herein as PcFc$_\epsilon$R$\alpha$4$_{253}$, having amino acid sequence SEQ ID NO: 20, assuming an open reading frame in which the initiation codon spans from about nucleotide 35 through about nucleotide 37 of SEQ ID NO: 19 and the termination codon spans from about nucleotide 794 through about nucleotide 796 of SEQ ID NO: 19. The complement of SEQ ID NO: 20 is represented herein by SEQ ID NO: 21. The coding region encoding PcFc$_\epsilon$R$\alpha$4$_{253}$, is represented by nucleic acid molecule ncFc$_\epsilon$R$\alpha$4$_{759}$, having a coding strand with the nucleic acid sequence represented by SEQ ID NO: 22 and a complementary strand with nucleic acid sequence SEQ ID NO: 23. The amino acid sequence of PcFc$_\epsilon$R$\alpha$$_{253}$ (i.e., SEQ ID NO: 21) predicts that PcFc$_\epsilon$R$\alpha$$_{253}$ has an estimated molecular weight of about 28.5 kD and an estimated pI of about 9.62.

Analysis of SEQ ID NO: 20 suggests the presence of a signal peptide encoded by a stretch of amino acids spanning from about amino acid 1 through about amino acid 24. The proposed mature protein, denoted herein as PcFc$_\epsilon$R$\alpha$4$_{229}$, contains about 229 amino acids, the sequence of which is shown as SEQ ID NO: 24. The coding strand encoding PcFc$_\epsilon$R$\alpha$4$_{229}$ is represented herein as SEQ ID NO: 30. The amino acid sequence of PcFc$_\epsilon$R$\alpha$4$_{229}$ (i.e., SEQ ID NO: 24) predicts that PcFc$_\epsilon$R$\alpha$4$_{229}$ has an estimated molecular weight of about 26 kD, an estimated pI of about 9.65 and five predicted asparagine-linked glycosylation sites extending from about amino acids 29–31, 42–44, 71–73, 135–137 and 148–150, respectively.

Comparison of amino acid sequence SEQ ID NO: 20 with amino acid sequences reported in GenBank indicates that SEQ ID NO: 20 showed the most homology, i.e., about 100% identity between SEQ ID NO: 20 and a *Canis canis* Fc$_\epsilon$R $\alpha$ chain protein (GenBank accession number D16413). Comparison of amino acid sequence SEQ ID NO: 22 with nucleic acid sequences reported in GenBank indicates that SEQ ID NO: 22 showed the most homology, i.e., about 100% identity between SEQ ID NO: 22 and a canine mRNA for Fc$_\epsilon$R $\alpha$ chain (GenBank accession D16413).

Example 5

This Example demonstrates the production of secreted canine Fc$_\epsilon$R $\alpha$ chain protein in eukaryotic cells.

To produce a secreted form of a canine Fc$_\epsilon$R $\alpha$ chain, recombinant molecule pVL-ncFc$_\epsilon$R$\alpha$4$_{591}$, containing a canine Fc$_\epsilon$R $\alpha$ chain nucleic acid molecule encoding a secreted form of canine Fc$_\epsilon$R $\alpha$ chain spanning nucleotides from about 35 through about 625 of SEQ ID NO: 19 operatively linked to baculovirus polyhedron transcription control sequences, was produced in the following manner. A canine Fc$_\epsilon$R $\alpha$ chain nucleic acid molecule of about 591 nucleotides was PCR amplified from ncFc$_\epsilon$R$\alpha$4$_{991}$ DNA using a sense primer canIgEr FWD having the nucleic acid sequence 5' GCG AAG ATC TAT AAA TAT GCC TGC TTC CAT GGG-3' (SEQ ID NO: 25; BglII site shown in bold) and an antisense primer canIgEr REV having the nucleic acid sequence 5' GCA GGA ATT CTT ACT CTT TTT TCA CAA TAA TGT-3' (SEQ ID NO: 26; EcoRI site shown in bold). The N-terminal primer was designed from the pol h sequence of baculovirus with modifications to enhance expression in the baculovirus system.

The about 591 base pair PCR product (referred to as ncFc$_\epsilon$R$\alpha$4$_{591}$) has a coding strand nucleic acid sequence denoted herein as SEQ ID NO: 27. The complement of SEQ ID NO: 27 is represented herein by SEQ ID NO: 29. Translation of SEQ ID NO: 27 indicates that nucleic acid molecule ncFc$_\epsilon$Rα4$_{591}$ encodes a Fc$_\epsilon$R α chain protein of about 197 amino acids, referred to herein as PcFc$_\epsilon$Rα4$_{197}$, having amino acid sequence SEQ ID NO: 28. Nucleic acid molecule ncFc$_\epsilon$Rα$_{591}$ encodes a secretable form of the canine Fc$_\epsilon$R α chain. The processed protein product encoded by ncFc$_\epsilon$Rα4$_{591}$ does not possess a leader sequence or transmembrane domain, and is referred to herein as PcFc$_\epsilon$Rα4$_{173}$, represented herein by SEQ ID NO: 31.

Nucleic acid molecule Bv-ncFc$_\epsilon$Rα$_{591}$ was digested with BglII and EcoRI and subcloned into the unique BglII and EcoRI sites of baculovirus shuttle plasmid pVL1392 (available from Pharmingen, San Diego, Calif.) to produce the recombinant molecule referred to herein as pVL-ncFc$_\epsilon$Rα$_{591}$. The resultant recombinant molecule, pVL-ncFc$_\epsilon$Rα$_{591}$, was verified for proper insert orientation by restriction mapping. The recombinant molecule pVL-ncFc$_\epsilon$Rα$_{591}$ was co-transfected with a Baculogold™ baculovirus DNA into S. frugiperda Sf9 cells (available from Invitrogen) to form recombinant cells denoted S. frugiperda:pVL-ncFc$_\epsilon$Rα$_{591}$. Recombinant baculovirus was plaque purified and amplified from each transfection by methods well known to those skilled in the art, to produce recombinant baculovirus BV-ncFc$_\epsilon$Rα$_{591}$.

S. frugiperda:pVL-ncFc$_\epsilon$Rα$_{591}$ cells were cultured in order to produce a secreted canine Fc$_\epsilon$R α chain protein, PcFc$_\epsilon$Rα4$_{197}$ in the following manner. An about 1.5 liter cultures of serum-free ex-Cell Medium was seeded with about 1×10$^6$ Trichoplusia ni cells (High Five™ cells) per ml of medium. The cell culture was inoculated with recombinant baculovirus BV-ncFc$_\epsilon$Rα$_{591}$ at a multiplicity of infection (MOI) of about 2 to about 5 plaque forming units (pfu) per cell to produce recombinant cell Trichoplusia ni:BV-ncFc$_\epsilon$Rα$_{591}$. The infection was allowed to proceed at a controlled temperature of 27° C. for 48 hours, to produce recombinant protein of PcFc$_\epsilon$Rα$_{197}$. Following infection, cells were separated from the medium by centrifugation, and the medium was frozen at −70° C.

SEQUENCE LISTING (1) GENERAL INFORMATION:

(iii) NUMBER OF SEQUENCES: 31

(2) INFORMATION FOR SEQ ID NO:1:

(i) SEQUENCE CHARACTERISTICS:
      (A) LENGTH: 30 nucleotides
      (B) TYPE: nucleic acid
      (C) STRANDEDNESS: single
      (D) TOPOLOGY: linear (ii) MOLECULE TYPE: primer (xi) SEQUENCE DESCRIPTION: SEQ ID NO:1:

TGCGGATCCA ATATGCCTGC TTCCATGGGA                    30

(2) INFORMATION FOR SEQ ID NO:2:

(i) SEQUENCE CHARACTERISTICS:
      (A) LENGTH: 34 nucleotides
      (B) TYPE: nucleic acid
      (C) STRANDEDNESS: single
      (D) TOPOLOGY: linear (ii) MOLECULE TYPE: primer (xi) SEQUENCE DESCRIPTION: SEQ ID NO:2:

TTGGAATTCT TACTCTTTTT TCACAATAAT GTTG                34

(2) INFORMATION FOR SEQ ID NO:3:

(i) SEQUENCE CHARACTERISTICS:
      (A) LENGTH: 609 nucleotides
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 10..603

(ix) FEATURE:
      (A) NAME/KEY: R = A or G (B) LOCATION: 188

(ix) FEATURE:
 (A) NAME/KEY: Xaa = unknown amino acid
 (B) LOCATION: 60

(xi) SEQUENCE DESCRIPTION: SEQ ID NO:3:

```
GGATCCAAT ATG CCT GCT TCC ATG GGA GGC CCT GCC CTG CTG              42
          Met Pro Ala Ser Met Gly Gly Pro Ala Leu Leu
          1               5                   10

TGG CTA GCG CTG CTG CTC TCC TCT CCA GGT GTC ATG TCA TCA             84
Trp Leu Ala Leu Leu Leu Ser Ser Pro Gly Val Met Ser Ser
            15                  20                  25

GAT ACC TTG AAA CCT ACA GTG TCC ATG AAC CCG CCA TGG AAT            126
Asp Thr Leu Lys Pro Thr Val Ser Met Asn Pro Pro Trp Asn
                30                  35

ACA ATA TTG AAG GAT GAC AGT GTG ACT CTT ACA TGT ACT GGG            168
Thr Ile Leu Lys Asp Asp Ser Val Thr Leu Thr Cys Thr Gly
40                  45                  50

AAC AAC TCC CTT GAA GTC GRC TCT GCT GTG TGG CTC CAC AAC            210
Asn Asn Ser Leu Glu Val Xaa Ser Ala Val Trp Leu His Asn
    55                  60                  65

AAC ACT ACT TTG CAA GAG ACG ACT TCA CGT TTG GAC ATC AAT            252
Asn Thr Thr Leu Gln Glu Thr Thr Ser Arg Leu Asp Ile Asn
        70                  75                  80

AAA GCC CAA ATC CAG GAC AGT GGG GAG TAC AGG TGT CGG GAA            294
Lys Ala Gln Ile Gln Asp Ser Gly Glu Tyr Arg Cys Arg Glu
            85                  90                  95

AAT AGA TCC ATC CTG AGT GAT CCT GTG TAC CTA ACA GTC TTC            336
Asn Arg Ser Ile Leu Ser Asp Pro Val Tyr Leu Thr Val Phe
                100                 105

ACA GAG TGG CTG ATC CTT CAA GCC TCT GCC AAC GTG GTG ATG            378
Thr Glu Trp Leu Ile Leu Gln Ala Ser Ala Asn Val Val Met
110                 115                 120

GAG GGT GAG AGC TTC CTC ATC AGG TGC CAT AGT TGG AAG AAT            420
Glu Gly Glu Ser Phe Leu Ile Arg Cys His Ser Trp Lys Asn
    125                 130                 135

TTG AGG CTC ACA AAG GTG ACC TAC TAC AAG GAT GGC ATC CCC            462
Leu Arg Leu Thr Lys Val Thr Tyr Tyr Lys Asp Gly Ile Pro
        140                 145                 150

ATC AGG TAC TGG TAC GAG AAC TTC AAC ATC TCC ATT AGC AAC            504
Ile Arg Tyr Trp Tyr Glu Asn Phe Asn Ile Ser Ile Ser Asn
            155                 160                 165

GTC ACA ACC AAA AAC AGC GGC AAC TAT TCC TGC TCA GGC CAG            546
Val Thr Thr Lys Asn Ser Gly Asn Tyr Ser Cys Ser Gly Gln
                170                 175

ATC CAG CAG AAA GGC TAC ACC TCT AAA GTC CTC AAC ATT ATT            588
Ile Gln Gln Lys Gly Tyr Thr Ser Lys Val Leu Asn Ile Ile
180                 185                 190

GTG AAA AAA GAG TAA GAATTC                                         609
Val Lys Lys Glu
    195
```

(2) INFORMATION FOR SEQ ID NO:4:

(i) SEQUENCE CHARACTERISTICS:
  (A) LENGTH: 197 amino acids
  (B) TYPE: amino acid
  (D) TOPOLOGY: linear (ii) MOLECULE TYPE: protein (ix) FEATURE:

(A) NAME/KEY: Xaa = unknown amino acid
(B) LOCATION: 60

(xi) SEQUENCE DESCRIPTION: SEQ ID NO:4:

```
Met Pro Ala Ser Met Gly Gly Pro Ala Leu Leu Trp Leu Ala
 1               5                  10
Leu Leu Leu Ser Ser Pro Gly Val Met Ser Ser Asp Thr Leu
15                  20                  25
Lys Pro Thr Val Ser Met Asn Pro Pro Trp Asn Thr Ile Leu
        30                  35                  40
Lys Asp Asp Ser Val Thr Leu Thr Cys Thr Gly Asn Asn Ser
            45                  50                  55
Leu Glu Val Xaa Ser Ala Val Trp Leu His Asn Asn Thr Thr
                60                  65                  70
Leu Gln Glu Thr Thr Ser Arg Leu Asp Ile Asn Lys Ala Gln
                    75                  80
Ile Gln Asp Ser Gly Glu Tyr Arg Cys Arg Glu Asn Arg Ser
85                  90                  95
Ile Leu Ser Asp Pro Val Tyr Leu Thr Val Phe Thr Glu Trp
        100                 105                 110
Leu Ile Leu Gln Ala Ser Ala Asn Val Val Met Glu Gly Glu
            115                 120                 125
Ser Phe Leu Ile Arg Cys His Ser Trp Lys Asn Leu Arg Leu
                130                 135                 140
Thr Lys Val Thr Tyr Tyr Lys Asp Gly Ile Pro Ile Arg Tyr
                    145                 150
Trp Tyr Glu Asn Phe Asn Ile Ser Ile Ser Asn Val Thr Thr
155                 160                 165
Lys Asn Ser Gly Asn Tyr Ser Cys Ser Gly Gln Ile Gln Gln
        170                 175                 180
Lys Gly Tyr Thr Ser Lys Val Leu Asn Ile Ile Val Lys Lys
            185                 190                 195
Glu
```

(2) INFORMATION FOR SEQ ID NO:5:

(i) SEQUENCE CHARACTERISTICS:
(A) LENGTH: 609 nucleotides
(B) TYPE: nucleic acid
(C) STRANDEDNESS: single
(D) TOPOLOGY: linear (ii) MOLECULE TYPE: cDNA (ix) FEATURE:
(A) NAME/KEY: Y = G or T
(B) LOCATION: 422

(xi) SEQUENCE DESCRIPTION: SEQ ID NO:5:

```
GAATTCTTAC TCTTTTTTCA CAATAATGTT GAGGACTTTA GAGGTGTAGC           50
CTTTCTGCTG GATCTGGCCT GAGCAGGAAT AGTTGCCGCT GTTTTTGGTT          100
GTGACGTTGC TAATGGAGAT GTTGAAGTTC TCGTACCAGT ACCTGATGGG          150
GATGCCATCC TTGTAGTAGG TCACCTTTGT GAGCCTCAAA TTCTTCCAAC          200
TATGGCACCT GATGAGGAAG CTCTCACCCT CCATCACCAC GTTGGCAGAG          250
GCTTGAAGGA TCAGCCACTC TGTGAAGACT GTTAGGTACA CAGGATCACT          300
CAGGATGGAT CTATTTTCCC GACACCTGTA CTCCCCACTG TCCTGGATTT          350
```

```
GGGCTTTATT GATGTCCAAA CGTGAAGTCG TCTCTTGCAA AGTAGTGTTG            400

TTGTGGAGCC ACACAGCAGA GYCGACTTCA AGGGAGTTGT TCCCAGTACA            450

TGTAAGAGTC ACACTGTCAT CCTTCAATAT TGTATTCCAT GGCGGGTTCA            500

TGGACACTGT AGGTTTCAAG GTATCTGATG ACATGACACC TGGAGAGGAG            550

AGCAGCAGCG CTAGCCACAG CAGGGCAGGG CCTCCCATGG AAGCAGGCAT            600

ATTGGATCC                                                         609

(2) INFORMATION FOR SEQ ID NO:6:

(i) SEQUENCE CHARACTERISTICS:
        (A) LENGTH: 591 nucleotides
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..591

(ix) FEATURE:
        (A) NAME/KEY: R = A or G
        (B) LOCATION: 179

(ix) FEATURE:
        (A) NAME/KEY: Xaa = unknown amino acid
        (B) LOCATION: 60

(xi) SEQUENCE DESCRIPTION: SEQ ID NO:6:

ATG CCT GCT TCC ATG GGA GGC CCT GCC CTG CTG TGG CTA GCG            42
Met Pro Ala Ser Met Gly Gly Pro Ala Leu Leu Trp Leu Ala
1               5                   10

CTG CTG CTC TCC TCT CCA GGT GTC ATG TCA TCA GAT ACC TTG            84
Leu Leu Leu Ser Ser Pro Gly Val Met Ser Ser Asp Thr Leu
15                  20                  25

AAA CCT ACA GTG TCC ATG AAC CCG CCA TGG AAT ACA ATA TTG           126
Lys Pro Thr Val Ser Met Asn Pro Pro Trp Asn Thr Ile Leu
30                  35                  40

AAG GAT GAC AGT GTG ACT CTT ACA TGT ACT GGG AAC AAC TCC           168
Lys Asp Asp Ser Val Thr Leu Thr Cys Thr Gly Asn Asn Ser
45                  50                  55

CTT GAA GTC GRC TCT GCT GTG TGG CTC CAC AAC AAC ACT ACT           210
Leu Glu Val Xaa Ser Ala Val Trp Leu His Asn Asn Thr Thr
60                  65                  70

TTG CAA GAG ACG ACT TCA CGT TTG GAC ATC AAT AAA GCC CAA           252
Leu Gln Glu Thr Thr Ser Arg Leu Asp Ile Asn Lys Ala Gln
75                  80

ATC CAG GAC AGT GGG GAG TAC AGG TGT CGG GAA AAT AGA TCC           294
Ile Gln Asp Ser Gly Glu Tyr Arg Cys Arg Glu Asn Arg Ser
85                  90                  95

ATC CTG AGT GAT CCT GTG TAC CTA ACA GTC TTC ACA GAG TGG           336
Ile Leu Ser Asp Pro Val Tyr Leu Thr Val Phe Thr Glu Trp
100                 105                 110

CTG ATC CTT CAA GCC TCT GCC AAC GTG GTG ATG GAG GGT GAG           378
Leu Ile Leu Gln Ala Ser Ala Asn Val Val Met Glu Gly Glu
115                 120                 125

AGC TTC CTC ATC AGG TGC CAT AGT TGG AAG AAT TTG AGG CTC           420
Ser Phe Leu Ile Arg Cys His Ser Trp Lys Asn Leu Arg Leu
130                 135                 140

ACA AAG GTG ACC TAC TAC AAG GAT GGC ATC CCC ATC AGG TAC           462
```

```
Thr Lys Val Thr Tyr Tyr Lys Asp Gly Ile Pro Ile Arg Tyr
145                 150

TGG TAC GAG AAC TTC AAC ATC TCC ATT AGC AAC GTC ACA ACC        504
Trp Tyr Glu Asn Phe Asn Ile Ser Ile Ser Asn Val Thr Thr
155                 160                 165

AAA AAC AGC GGC AAC TAT TCC TGC TCA GGC CAG ATC CAG CAG        546
Lys Asn Ser Gly Asn Tyr Ser Cys Ser Gly Gln Ile Gln Gln
170                 175                 180

AAA GGC TAC ACC TCT AAA GTC CTC AAC ATT ATT GTG AAA AAA        588
Lys Gly Tyr Thr Ser Lys Val Leu Asn Ile Ile Val Lys Lys
185                 190                 195

GAG                                                            591
Glu (2) INFORMATION FOR SEQ ID NO:7:

(i) SEQUENCE CHARACTERISTICS:
        (A) LENGTH:  591 nucleotides
        (B) TYPE:  nucleic acid
        (C) STRANDEDNESS:  single
        (D) TOPOLOGY:  linear (ii) MOLECULE TYPE:  cDNA (ix) FEATURE:
        (A) NAME/KEY:  Y = C or T
        (B) LOCATION:  413

(xi) SEQUENCE DESCRIPTION:  SEQ ID NO:7:

CTCTTTTTTC ACAATAATGT TGAGGACTTT AGAGGTGTAG CCTTTCTGCT          50

GGATCTGGCC TGAGCAGGAA TAGTTGCCGC TGTTTTTGGT TGTGACGTTG         100

CTAATGGAGA TGTTGAAGTT CTCGTACCAG TACCTGATGG GGATGCCATC         150

CTTGTAGTAG GTCACCTTTG TGAGCCTCAA ATTCTTCCAA CTATGGCACC         200

TGATGAGGAA GCTCTCACCC TCCATCACCA CGTTGGCAGA GGCTTGAAGG         250

ATCAGCCACT CTGTGAAGAC TGTTAGGTAC ACAGGATCAC TCAGGATGGA         300

TCTATTTTCC CGACACCTGT ACTCCCCACT GTCCTGGATT TGGGCTTTAT         350

TGATGTCCAA ACGTGAAGTC GTCTCTTGCA AGTAGTGTT GTTGTGGAGC          400

CACACAGCAG AGYCGACTTC AAGGGAGTTG TTCCCAGTAC ATGTAAGAGT         450

CACACTGTCA TCCTTCAATA TTGTATTCCA TGGCGGGTTC ATGGACACTG         500

TAGGTTTCAA GGTATCTGAT GACATGACAC CTGGAGAGGA GAGCAGCAGC         550

GCTAGCCACA GCAGGGCAGG GCCTCCCATG GAAGCAGGCA T                  591

(2) INFORMATION FOR SEQ ID NO:8:

(i) SEQUENCE CHARACTERISTICS:
        (A) LENGTH:  609 nucleotides
        (B) TYPE:  nucleic acid
        (C) STRANDEDNESS:  single
        (D) TOPOLOGY:  linear (ii) MOLECULE TYPE:  cDNA (ix) FEATURE:
        (A) NAME/KEY:  CDS
        (B) LOCATION:  10..604

(ix) FEATURE:
        (A) NAME/KEY:  Xaa = unknown amino acid
        (B) LOCATION:  60, 195, 196

(ix) FEATURE:
```

```
            (A) NAME/KEY: K = G or T
            (B) LOCATION: 188

(ix) FEATURE:
            (A) NAME/KEY: N = unknown nucleotide
            (B) LOCATION: 592, 595, 596

(xi) SEQUENCE DESCRIPTION: SEQ ID NO:8:

GGATCCAAT ATG CCT GCT TCC ATG GGA GGC CCT GCC CTG CTG                    42
          Met Pro Ala Ser Met Gly Gly Pro Ala Leu Leu
            1               5                  10

TGG CTA GCG CTG CTG CTC TCC TCT CCA GGT GTC ATG TCA TCA                  84
Trp Leu Ala Leu Leu Leu Ser Ser Pro Gly Val Met Ser Ser
            15                  20                  25

GAT ACC TTG AAA CCT ACA GTG TCC ATG AAC CCG CCA TGG AAT                 126
Asp Thr Leu Lys Pro Thr Val Ser Met Asn Pro Pro Trp Asn
                30                  35

ACA ATA TTG AAG GAT GAC AGT GTG ACT CTT ACA TGT ACT GGG                 168
Thr Ile Leu Lys Asp Asp Ser Val Thr Leu Thr Cys Thr Gly
 40              45                  50

AAC AAC TCC CTT GAA GTC GKC TCT GCT GTG TGG CTC CAC AAC                 210
Asn Asn Ser Leu Glu Val Xaa Ser Ala Val Trp Leu His Asn
     55                  60                  65

AAC ACT ACT TTG CAA GAG ACG ACT TCA CGT TTG GAC ATC AAT                 252
Asn Thr Thr Leu Gln Glu Thr Thr Ser Arg Leu Asp Ile Asn
         70                  75                  80

AAA GCC CAA ATC CAG GAC AGT GGG GAG TAC AGG TGT CGG GAA                 294
Lys Ala Gln Ile Gln Asp Ser Gly Glu Tyr Arg Cys Arg Glu
             85                  90                  95

AAT AGA TCC ATC CTG AGT GAT CCT GTG TAC CTA ACA GTC TTC                 336
Asn Arg Ser Ile Leu Ser Asp Pro Val Tyr Leu Thr Val Phe
                100                 105

ACA GAG TGG CTG ATC CTT CAA GCC TCT GCC AAC GTG GTG ATG                 378
Thr Glu Trp Leu Ile Leu Gln Ala Ser Ala Asn Val Val Met
110                 115                 120

GAG GGT GAG AGC TTC CTC ATC AGG TGC CAT AGT TGG AAG AAT                 420
Glu Gly Glu Ser Phe Leu Ile Arg Cys His Ser Trp Lys Asn
        125                 130                 135

TTG AGG CTC ACA AAG GTG ACC TAC TAC AAG GAT GGC ATC CCC                 462
Leu Arg Leu Thr Lys Val Thr Tyr Tyr Lys Asp Gly Ile Pro
            140                 145                 150

ATC AGG TAC TGG TAC GAG AAC TTC AAC ATC TCC ATT AGC AAC                 504
Ile Arg Tyr Trp Tyr Glu Asn Phe Asn Ile Ser Ile Ser Asn
                155                 160                 165

GTC ACA ACC AAA AAC AGC GGC AAC TAT TCC TGC TCA GGC CAG                 546
Val Thr Thr Lys Asn Ser Gly Asn Tyr Ser Cys Ser Gly Gln
                    170                 175

ATC CAG CAG AAA GGC TAC ACC TCT AAA GTC CTC AAC ATT ATT                 588
Ile Gln Gln Lys Gly Tyr Thr Ser Lys Val Leu Asn Ile Ile
180                 185                 190

GTG NAA NNA GAG TAA GAATTC                                              609
Val Xaa Xaa Glu
    195

(2) INFORMATION FOR SEQ ID NO:9:

(i) SEQUENCE CHARACTERISTICS:
            (A) LENGTH: 197 amino acids
            (B) TYPE: amino acids
            (D) TOPOLOGY: linear (ii) MOLECULE TYPE: protein
```

(ix) FEATURE:
    (A) NAME/KEY: Xaa = unknown amino acid
    (B) LOCATION: 60, 195, 196

(xi) SEQUENCE DESCRIPTION: SEQ ID NO:9:

```
Met Pro Ala Ser Met Gly Gly Pro Ala Leu Leu Trp Leu Ala
1               5                   10
Leu Leu Leu Ser Ser Pro Gly Val Met Ser Ser Asp Thr Leu
15                  20                  25
Lys Pro Thr Val Ser Met Asn Pro Pro Trp Asn Thr Ile Leu
        30                  35                  40
Lys Asp Asp Ser Val Thr Leu Thr Cys Thr Gly Asn Asn Ser
            45                  50                  55
Leu Glu Val Xaa Ser Ala Val Trp Leu His Asn Asn Thr Thr
                60                  65                  70
Leu Gln Glu Thr Thr Ser Arg Leu Asp Ile Asn Lys Ala Gln
                    75                  80
Ile Gln Asp Ser Gly Glu Tyr Arg Cys Arg Glu Asn Arg Ser
85                  90                  95
Ile Leu Ser Asp Pro Val Tyr Leu Thr Val Phe Thr Glu Trp
        100                 105                 110
Leu Ile Leu Gln Ala Ser Ala Asn Val Val Met Glu Gly Glu
            115                 120                 125
Ser Phe Leu Ile Arg Cys His Ser Trp Lys Asn Leu Arg Leu
                130                 135                 140
Thr Lys Val Thr Tyr Tyr Lys Asp Gly Ile Pro Ile Arg Tyr
                    145                 150
Trp Tyr Glu Asn Phe Asn Ile Ser Ile Ser Asn Val Thr Thr
155                 160                 165
Lys Asn Ser Gly Asn Tyr Ser Cys Ser Gly Gln Ile Gln Gln
        170                 175                 180
Lys Gly Tyr Thr Ser Lys Val Leu Asn Ile Ile Val Xaa Xaa
            185                 190                 195
Glu
```

(2) INFORMATION FOR SEQ ID NO:10:

(i) SEQUENCE CHARACTERISTICS:
        (A) LENGTH: 609 nucleotides
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: N = any nucleotide
        (B) LOCATION: 14, 15, 18

(ix) FEATURE:
        (A) NAME/KEY: M = A or C
        (B) LOCATION: 422

(xi) SEQUENCE DESCRIPTION: SEQ ID NO:10:

```
GAATTCTTAC TCTNNTTNCA CAATAATGTT GAGGACTTTA GAGGTGTAGC            50

CTTTCTGCTG GATCTGGCCT GAGCAGGAAT AGTTGCCGCT GTTTTTGGTT           100

GTGACGTTGC TAATGGAGAT GTTGAAGTTC TCGTACCAGT ACCTGATGGG           150

GATGCCATCC TTGTAGTAGG TCACCTTTGT GAGCCTCAAA TTCTTCCAAC           200
```

| TATGGCACCT GATGAGGAAG CTCTCACCCT CCATCACCAC GTTGGCAGAG | 250 |
| GCTTGAAGGA TCAGCCACTC TGTGAAGACT GTTAGGTACA CAGGATCACT | 300 |
| CAGGATGGAT CTATTTTCCC GACACCTGTA CTCCCCACTG TCCTGGATTT | 350 |
| GGGCTTTATT GATGTCCAAA CGTGAAGTCG TCTCTTGCAA AGTAGTGTTG | 400 |
| TTGTGGAGCC ACACAGCAGA GMCGACTTCA AGGGAGTTGT TCCCAGTACA | 450 |
| TGTAAGAGTC ACACTGTCAT CCTTCAATAT TGTATTCCAT GGCGGGTTCA | 500 |
| TGGACACTGT AGGTTTCAAG GTATCTGATG ACATGACACC TGGAGAGGAG | 550 |
| AGCAGCAGCG CTAGCCACAG CAGGGCAGGG CCTCCCATGG AAGCAGGCAT | 600 |
| ATTGGATCC | 609 |

(2) INFORMATION FOR SEQ ID NO:11:

(i) SEQUENCE CHARACTERISTICS:
        (A) LENGTH: 591 nucleotides
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Xaa = unknown amino acid
        (B) LOCATION: 60, 195, 196

(ix) FEATURE:
        (A) NAME/KEY: K = G or T
        (B) LOCATION: 179

(ix) FEATURE:
        (A) NAME/KEY: N = unknown nucleotide
        (B) LOCATION: 583, 586, 587

(ix) FEATURE:
        (A) NAME/KEY: CDS
        (B) LOCATION: 1..591

(xi) SEQUENCE DESCRIPTION: SEQ ID NO:11:

| ATG CCT GCT TCC ATG GGA GGC CCT GCC CTG CTG TGG CTA GCG | 42 |
| Met Pro Ala Ser Met Gly Gly Pro Ala Leu Leu Trp Leu Ala | |
| 1                5                    10 | |
| CTG CTG CTC TCC TCT CCA GGT GTC ATG TCA TCA GAT ACC TTG | 84 |
| Leu Leu Leu Ser Ser Pro Gly Val Met Ser Ser Asp Thr Leu | |
| 15               20               25 | |
| AAA CCT ACA GTG TCC ATG AAC CCG CCA TGG AAT ACA ATA TTG | 126 |
| Lys Pro Thr Val Ser Met Asn Pro Pro Trp Asn Thr Ile Leu | |
| 30               35                   40 | |
| AAG GAT GAC AGT GTG ACT CTT ACA TGT ACT GGG AAC AAC TCC | 168 |
| Lys Asp Asp Ser Val Thr Leu Thr Cys Thr Gly Asn Asn Ser | |
|         45               50                  55 | |
| CTT GAA GTC GKC TCT GCT GTG TGG CTC CAC AAC AAC ACT ACT | 210 |
| Leu Glu Val Xaa Ser Ala Val Trp Leu His Asn Asn Thr Thr | |
|             60               65                  70 | |
| TTG CAA GAG ACG ACT TCA CGT TTG GAC ATC AAT AAA GCC CAA | 252 |
| Leu Gln Glu Thr Thr Ser Arg Leu Asp Ile Asn Lys Ala Gln | |
|                  75                    80 | |
| ATC CAG GAC AGT GGG GAG TAC AGG TGT CGG GAA AAT AGA TCC | 294 |
| Ile Gln Asp Ser Gly Glu Tyr Arg Cys Arg Glu Asn Arg Ser | |
| 85               90                    95 | |
| ATC CTG AGT GAT CCT GTG TAC CTA ACA GTC TTC ACA GAG TGG | 336 |
| Ile Leu Ser Asp Pro Val Tyr Leu Thr Val Phe Thr Glu Trp | |
|     100              105              110 | |

```
CTG ATC CTT CAA GCC TCT GCC AAC GTG GTG ATG GAG GGT GAG      378
Leu Ile Leu Gln Ala Ser Ala Asn Val Val Met Glu Gly Glu
        115                 120                 125

AGC TTC CTC ATC AGG TGC CAT AGT TGG AAG AAT TTG AGG CTC      420
Ser Phe Leu Ile Arg Cys His Ser Trp Lys Asn Leu Arg Leu
        130                 135                 140

ACA AAG GTG ACC TAC TAC AAG GAT GGC ATC CCC ATC AGG TAC      462
Thr Lys Val Thr Tyr Tyr Lys Asp Gly Ile Pro Ile Arg Tyr
                145                 150

TGG TAC GAG AAC TTC AAC ATC TCC ATT AGC AAC GTC ACA ACC      504
Trp Tyr Glu Asn Phe Asn Ile Ser Ile Ser Asn Val Thr Thr
155                 160                 165

AAA AAC AGC GGC AAC TAT TCC TGC TCA GGC CAG ATC CAG CAG      546
Lys Asn Ser Gly Asn Tyr Ser Cys Ser Gly Gln Ile Gln Gln
        170                 175                 180

AAA GGC TAC ACC TCT AAA GTC CTC AAC ATT ATT GTG NAA NNA      588
Lys Gly Tyr Thr Ser Lys Val Leu Asn Ile Ile Val Xaa Xaa
        185                 190                 195

GAG                                                          591
Glu
```

(2) INFORMATION FOR SEQ ID NO:12:

(i) SEQUENCE CHARACTERISTICS:
        (A) LENGTH: 591 nucleotides
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: N = any nucleotide
        (B) LOCATION: 5, 6, 9

(ix) FEATURE:
        (A) NAME/KEY: M = A or C
        (B) LOCATION: 413

(xi) SEQUENCE DESCRIPTION: SEQ ID NO:12:

```
CTCTNNTTNC ACAATAATGT TGAGGACTTT AGAGGTGTAG CCTTTCTGCT       50

GGATCTGGCC TGAGCAGGAA TAGTTGCCGC TGTTTTTGGT TGTGACGTTG      100

CTAATGAGA TGTTGAAGTT CTCGTACCAG TACCTGATGG GGATGCCATC       150

CTTGTAGTAG GTCACCTTTG TGAGCCTCAA ATTCTTCCAA CTATGGCACC      200

TGATGAGGAA GCTCTCACCC TCCATCACCA CGTTGGCAGA GGCTTGAAGG      250

ATCAGCCACT CTGTGAAGAC TGTTAGGTAC ACAGGATCAC TCAGGATGGA      300

TCTATTTTCC CGACACCTGT ACTCCCCACT GTCCTGGATT TGGGCTTTAT      350

TGATGTCCAA ACGTGAAGTC GTCTCTTGCA AAGTAGTGTT GTTGTGGAGC      400

CACACAGCAG AGMCGACTTC AAGGGAGTTG TTCCCAGTAC ATGTAAGAGT      450

CACACTGTCA TCCTTCAATA TTGTATTCCA TGGCGGGTTC ATGGACACTG      500

TAGGTTTCAA GGTATCTGAT GACATGACAC CTGGAGAGGA GAGCAGCAGC      550

GCTAGCCACA GCAGGGCAGG GCCTCCCATG GAAGCAGGCA T               591
```

(2) INFORMATION FOR SEQ ID NO:13:

(i) SEQUENCE CHARACTERISTICS:
        (A) LENGTH: 617 nucleotides
        (B) TYPE: nucleic acid (C) STRANDEDNESS: single
        (D) TOPOLOGY: linear (ii) MOLECULE TYPE: cDNA (ix) FEATURE:
        (A) NAME/KEY: CDS
        (B) LOCATION: 10..606

(xi) SEQUENCE DESCRIPTION: SEQ ID NO:13:

```
GGATCCAAT ATG CCT GCT TCC ATG GGA GGC CCT GCC CTG CTG                42
          Met Pro Ala Ser Met Gly Gly Pro Ala Leu Leu
          1               5                   10

TGG CTA GCG CTG CTG CTC TCC TCT CCA GGT GTC GTG TCA TCA               84
Trp Leu Ala Leu Leu Leu Ser Ser Pro Gly Val Val Ser Ser
            15                  20                  25

GAT ACC TTG AAA CCT ACA GTG TCC ATG AAC CCG CCA TGG AAT              126
Asp Thr Leu Lys Pro Thr Val Ser Met Asn Pro Pro Trp Asn
                30                  35

ACA ATA TTG AAG GAT GAC AGT GTG ACT CTT ACA TGT ACT GGG              168
Thr Ile Leu Lys Asp Asp Ser Val Thr Leu Thr Cys Thr Gly
40                  45                  50

AAC AAC TCC CTT GAA GTC GAC TCT GCT GTG TGG CTC CAC AAC              210
Asn Asn Ser Leu Glu Val Asp Ser Ala Val Trp Leu His Asn
        55                  60                  65

AAC ACT ACT TTG CAA GAG ACG ACT TCA CGT TTG AAC ATC AAT              252
Asn Thr Thr Leu Gln Glu Thr Thr Ser Arg Leu Asn Ile Asn
            70                  75                  80

AAA GCC CAA ATC CAG GAC AGT GGG GAG TAC AGG TGT CGG GAA              294
Lys Ala Gln Ile Gln Asp Ser Gly Glu Tyr Arg Cys Arg Glu
                85                  90                  95

AAT AGA TCC ATC CTG AGT GAT CCT GTG TAC CTA ACA GTC TTC              336
Asn Arg Ser Ile Leu Ser Asp Pro Val Tyr Leu Thr Val Phe
                    100                 105

ACA GAG TGG CTG ATC CTT CAA GCC TCT GCC AAC GTG GTG ATG              378
Thr Glu Trp Leu Ile Leu Gln Ala Ser Ala Asn Val Val Met
110                 115                 120

GAG GGT GAG AGC TTC CTC ATC AGG TGC CAT AGT TGG AAG AAT              420
Glu Gly Glu Ser Phe Leu Ile Arg Cys His Ser Trp Lys Asn
        125                 130                 135

TTG AGG CTC ACA AAG GTG ACC TAC TAC AAG GAT GGC ATC CCC              462
Leu Arg Leu Thr Lys Val Thr Tyr Tyr Lys Asp Gly Ile Pro
            140                 145                 150

ATC AGG TAC TGG TAC GAG AAC TTC AAC ATC TCC ATT AGC AAC              504
Ile Arg Tyr Trp Tyr Glu Asn Phe Asn Ile Ser Ile Ser Asn
                155                 160                 165

GTC ACA ACC AAA AAC AGC GGC AAC TAT TCC TGC TCA GGC CAG              546
Val Thr Thr Lys Asn Ser Gly Asn Tyr Ser Cys Ser Gly Gln
                    170                 175

ATC CAG CAG AAA GGC TAC ACC TCT AAA GTC CTC AAC ATT ATT              588
Ile Gln Gln Lys Gly Tyr Thr Ser Lys Val Leu Asn Ile Ile
180                 185                 190

GTG AAA AAG AGT AAG AAT TCTAAGAATT C                                 617
Val Lys Lys Ser Lys Asn
            195
```

(2) INFORMATION FOR SEQ ID NO:14:

(i) SEQUENCE CHARACTERISTICS:
        (A) LENGTH: 199 amino acids
        (B) TYPE: amino acid
        (D) TOPOLOGY: linear -continued (ii) MOLECULE TYPE: protein (xi) SEQUENCE DESCRIPTION: SEQ ID NO:14:

```
Met Pro Ala Ser Met Gly Gly Pro Ala Leu Leu Trp Leu Ala
 1               5                  10
Leu Leu Leu Ser Ser Pro Gly Val Val Ser Ser Asp Thr Leu
15                  20                  25
Lys Pro Thr Val Ser Met Asn Pro Pro Trp Asn Thr Ile Leu
        30              35                  40
Lys Asp Asp Ser Val Thr Leu Thr Cys Thr Gly Asn Asn Ser
        45                  50                  55
Leu Glu Val Asp Ser Ala Val Trp Leu His Asn Asn Thr Thr
            60                  65                  70
Leu Gln Glu Thr Thr Ser Arg Leu Asn Ile Asn Lys Ala Gln
                75                  80
Ile Gln Asp Ser Gly Glu Tyr Arg Cys Arg Glu Asn Arg Ser
85                  90                  95
Ile Leu Ser Asp Pro Val Tyr Leu Thr Val Phe Thr Glu Trp
    100                 105                 110
Leu Ile Leu Gln Ala Ser Ala Asn Val Val Met Glu Gly Glu
    115                 120                 125
Ser Phe Leu Ile Arg Cys His Ser Trp Lys Asn Leu Arg Leu
            130                 135                 140
Thr Lys Val Thr Tyr Tyr Lys Asp Gly Ile Pro Ile Arg Tyr
                145                 150
Trp Tyr Glu Asn Phe Asn Ile Ser Ile Ser Asn Val Thr Thr
155                 160                 165
Lys Asn Ser Gly Asn Tyr Ser Cys Ser Gly Gln Ile Gln Gln
    170                 175                 180
Lys Gly Tyr Thr Ser Lys Val Leu Asn Ile Ile Val Lys Lys
            185                 190                 195
Ser Lys Asn
```

(2) INFORMATION FOR SEQ ID NO:15:

(i) SEQUENCE CHARACTERISTICS:
(A) LENGTH: 617 nucleotides
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:15:

```
GAATTCTTAG AATTCTTACT CTTTTTCACA ATAATGTTGA GGACTTTAGA              50

GGTGTAGCCT TTCTGCTGGA TCTGGCCTGA GCAGGAATAG TTGCCGCTGT             100

TTTTGGTTGT GACGTTGCTA ATGGAGATGT TGAAGTTCTC GTACCAGTAC             150

CTGATGGGGA TGCCATCCTT GTAGTAGGTC ACCTTTGTGA GCCTCAAATT             200

CTTCCAACTA TGGCACCTGA TGAGGAAGCT CTCACCCTCC ATCACCACGT             250

TGGCAGAGGC TTGAAGGATC AGCCACTCTG TGAAGACTGT TAGGTACACA             300

GGATCACTCA GGATGGATCT ATTTTCCCGA CACCTGTACT CCCCACTGTC             350

CTGGATTTGG GCTTTATTGA TGTTCAAACG TGAAGTCGTC TCTTGCAAAG             400

TAGTGTTGTT GTGGAGCCAC ACAGCAGAGT CGACTTCAAG GGAGTTGTTC             450
```

```
CCAGTACATG TAAGAGTCAC ACTGTCATCC TTCAATATTG TATTCCATGG              500

CGGGTTCATG GACACTGTAG GTTTCAAGGT ATCTGATGAC ACGACACCTG              550

GAGAGGAGAG CAGCAGCGCT AGCCACAGCA GGGCAGGGCC TCCCATGGAA              600

GCAGGCATAT TGGATCC                                                  617
```

(2) INFORMATION FOR SEQ ID NO:16:

(i) SEQUENCE CHARACTERISTICS:
        (A) LENGTH: 597 nucleotides
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..597

(xi) SEQUENCE DESCRIPTION: SEQ ID NO:16:

```
ATG CCT GCT TCC ATG GGA GGC CCT GCC CTG CTG TGG CTA GCG              42
Met Pro Ala Ser Met Gly Gly Pro Ala Leu Leu Trp Leu Ala
 1               5                  10

CTG CTG CTC TCC TCT CCA GGT GTC GTG TCA TCA GAT ACC TTG              84
Leu Leu Leu Ser Ser Pro Gly Val Val Ser Ser Asp Thr Leu
15                  20                  25

AAA CCT ACA GTG TCC ATG AAC CCG CCA TGG AAT ACA ATA TTG             126
Lys Pro Thr Val Ser Met Asn Pro Pro Trp Asn Thr Ile Leu
        30                  35                  40

AAG GAT GAC AGT GTG ACT CTT ACA TGT ACT GGG AAC AAC TCC             168
Lys Asp Asp Ser Val Thr Leu Thr Cys Thr Gly Asn Asn Ser
                45                  50                  55

CTT GAA GTC GAC TCT GCT GTG TGG CTC CAC AAC AAC ACT ACT             210
Leu Glu Val Asp Ser Ala Val Trp Leu His Asn Asn Thr Thr
                    60                  65                  70

TTG CAA GAG ACG ACT TCA CGT TTG AAC ATC AAT AAA GCC CAA             252
Leu Gln Glu Thr Thr Ser Arg Leu Asn Ile Asn Lys Ala Gln
                        75                  80

ATC CAG GAC AGT GGG GAG TAC AGG TGT CGG GAA AAT AGA TCC             294
Ile Gln Asp Ser Gly Glu Tyr Arg Cys Arg Glu Asn Arg Ser
85                  90                  95

ATC CTG AGT GAT CCT GTG TAC CTA ACA GTC TTC ACA GAG TGG             336
Ile Leu Ser Asp Pro Val Tyr Leu Thr Val Phe Thr Glu Trp
        100                 105                 110

CTG ATC CTT CAA GCC TCT GCC AAC GTG GTG ATG GAG GGT GAG             378
Leu Ile Leu Gln Ala Ser Ala Asn Val Val Met Glu Gly Glu
                115                 120                 125

AGC TTC CTC ATC AGG TGC CAT AGT TGG AAG AAT TTG AGG CTC             420
Ser Phe Leu Ile Arg Cys His Ser Trp Lys Asn Leu Arg Leu
                    130                 135                 140

ACA AAG GTG ACC TAC TAC AAG GAT GGC ATC CCC ATC AGG TAC             462
Thr Lys Val Thr Tyr Tyr Lys Asp Gly Ile Pro Ile Arg Tyr
                        145                 150

TGG TAC GAG AAC TTC AAC ATC TCC ATT AGC AAC GTC ACA ACC             504
Trp Tyr Glu Asn Phe Asn Ile Ser Ile Ser Asn Val Thr Thr
155                 160                 165

AAA AAC AGC GGC AAC TAT TCC TGC TCA GGC CAG ATC CAG CAG             546
Lys Asn Ser Gly Asn Tyr Ser Cys Ser Gly Gln Ile Gln Gln
        170                 175                 180

AAA GGC TAC ACC TCT AAA GTC CTC AAC ATT ATT GTG AAA AAG             588
Lys Gly Tyr Thr Ser Lys Val Leu Asn Ile Ile Val Lys Lys
```

```
                185             190             195
AGT AAG AAT                                                              597
Ser Lys Asn (2) INFORMATION FOR SEQ ID NO:17:

(i) SEQUENCE CHARACTERISTICS:
        (A) LENGTH: 597 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

ATTCTTACTC TTTTTCACAA TAATGTTGAG GACTTTAGAG GTGTAGCCTT                     50

TCTGCTGGAT CTGGCCTGAG CAGGAATAGT TGCCGCTGTT TTTGGTTGTG                    100

ACGTTGCTAA TGGAGATGTT GAAGTTCTCG TACCAGTACC TGATGGGGAT                    150

GCCATCCTTG TAGTAGGTCA CCTTTGTGAG CCTCAAATTC TTCCAACTAT                    200

GGCACCTGAT GAGGAAGCTC TCACCCTCCA TCACCACGTT GGCAGAGGCT                    250

TGAAGGATCA GCCACTCTGT GAAGACTGTT AGGTACACAG GATCACTCAG                    300

GATGGATCTA TTTTCCCGAC ACCTGTACTC CCCACTGTCC TGGATTTGGG                    350

CTTTATTGAT GTTCAAACGT GAAGTCGTCT CTTGCAAAGT AGTGTTGTTG                    400

TGGAGCCACA CAGCAGAGTC GACTTCAAGG GAGTTGTTCC CAGTACATGT                    450

AAGAGTCACA CTGTCATCCT TCAATATTGT ATTCCATGGC GGGTTCATGG                    500

ACACTGTAGG TTTCAAGGTA TCTGATGACA CGACACCTGG AGAGGAGAGC                    550

AGCAGCGCTA GCCACAGCAG GGCAGGGCCT CCCATGGAAG CAGGCAT                       597

(2) INFORMATION FOR SEQ ID NO:18:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (ix) FEATURE:
        (A) NAME/KEY: Xaa = any amino acid
        (B) LOCATION: 9, 14

(xi) SEQUENCE DESCRIPTION: SEQ ID NO:18:

Ser Asp Thr Leu Lys Pro Thr Val Xaa Met Asn Pro Pro Xaa
1               5                   10

Asn Leu Ile
 15

(2) INFORMATION FOR SEQ ID NO:19:

(i) SEQUENCE CHARACTERISTICS:
        (A) LENGTH: 991 nucleotides
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 35..796

(xi) SEQUENCE DESCRIPTION: SEQ ID NO:19:
```

```
CTCCAGTCCA GTCGTACGTG GGGGCCACGA GGAG ATG CCT GCT                          43
                                    Met Pro Ala
                                     1

TCC ATG GGA GGC CCT GCC CTG CTG TGG CTA GCG CTG CTG CTC                    85
Ser Met Gly Gly Pro Ala Leu Leu Trp Leu Ala Leu Leu Leu
     5               10                  15

TCC TCT CCA GGT GTC ATG TCA TCA GAT ACC TTG AAA CCT ACA                    127
Ser Ser Pro Gly Val Met Ser Ser Asp Thr Leu Lys Pro Thr
        20                  25                  30

GTG TCC ATG AAC CCG CCA TGG AAT ACA ATA TTG AAG GAT GAC                    169
Val Ser Met Asn Pro Pro Trp Asn Thr Ile Leu Lys Asp Asp
            35                  40                  45

AGT GTG ACT CTT ACA TGT ACT GGG AAC AAC TCC CTT GAA GTC                    211
Ser Val Thr Leu Thr Cys Thr Gly Asn Asn Ser Leu Glu Val
                50                  55

GAC TCT GCT GTG TGG CTC CAC AAC AAC ACT ACT TTG CAA GAG                    253
Asp Ser Ala Val Trp Leu His Asn Asn Thr Thr Leu Gln Glu
60                  65                  70

ACG ACT TCA CGT TTG GAC ATC AAT AAA GCC CAA ATC CAG GAC                    295
Thr Thr Ser Arg Leu Asp Ile Asn Lys Ala Gln Ile Gln Asp
     75                  80                  85

AGT GGG GAG TAC AGG TGT CGG GAA AAT AGA TCC ATC CTG AGT                    337
Ser Gly Glu Tyr Arg Cys Arg Glu Asn Arg Ser Ile Leu Ser
        90                  95                 100

GAT CCT GTG TAC CTA ACA GTC TTC ACA GAG TGG CTG ATC CTT                    379
Asp Pro Val Tyr Leu Thr Val Phe Thr Glu Trp Leu Ile Leu
            105                 110                 115

CAA GCC TCT GCC AAC GTG GTG ATG GAG GGT GAG AGC TTC CTC                    421
Gln Ala Ser Ala Asn Val Val Met Glu Gly Glu Ser Phe Leu
                120                 125

ATC AGG TGC CAT AGT TGG AAG AAT TTG AGG CTC ACA AAG GTG                    463
Ile Arg Cys His Ser Trp Lys Asn Leu Arg Leu Thr Lys Val
130                 135                 140

ACC TAC TAC AAG GAT GGC ATC CCC ATC AGG TAC TGG TAC GAG                    505
Thr Tyr Tyr Lys Asp Gly Ile Pro Ile Arg Tyr Trp Tyr Glu
     145                 150                 155

AAC TTC AAC ATC TCC ATT AGC AAC GTC ACA ACC AAA AAC AGC                    547
Asn Phe Asn Ile Ser Ile Ser Asn Val Thr Thr Lys Asn Ser
        160                 165                 170

GGC AAC TAT TCC TGC TCA GGC CAG ATC CAG CAG AAA GGC TAC                    589
Gly Asn Tyr Ser Cys Ser Gly Gln Ile Gln Gln Lys Gly Tyr
            175                 180                 185

ACC TCT AAA GTC CTC AAC ATT ATT GTG AAA AAA GAG CCC ACC                    631
Thr Ser Lys Val Leu Asn Ile Ile Val Lys Lys Glu Pro Thr
                190                 195

AAG CAA AAC AAG TAC TCC GGG CTA CAA TTC CTG ATC CCG TTG                    673
Lys Gln Asn Lys Tyr Ser Gly Leu Gln Phe Leu Ile Pro Leu
200                 205                 210

GTG GTG GTG ATT CTG TTT GCT GTG GAC ACA GGA CTG TTT ATC                    715
Val Val Val Ile Leu Phe Ala Val Asp Thr Gly Leu Phe Ile
     215                 220                 225

TCG ACC AAG CAG CAG TTG ACA GTG CTC TTG CAG ATT AAG AGG                    757
Ser Thr Lys Gln Gln Leu Thr Val Leu Leu Gln Ile Lys Arg
        230                 235                 240

ACC AGG AAG AAC AAA AAG CCA GAA CCC GGA AAG AAC TGA                        796
Thr Arg Lys Asn Lys Lys Pro Glu Pro Gly Lys Asn
            245                 250

TGCCGCTGCT TAAGAAACAT CAGCATCAGC AATCGCTTCT CCATCGTCAG                     846
```

```
ACGCAGCTCA CGATGCACAC GGGAAGGTCT GCAGTCATGG CTTTGCAGAA          896

CTGCTTCATT CAACCAACTC AAACTGATTA AGTGGCATGT GATAGTAGGT          946

GCTCAATAAA CGGCAGTTAG ATAAATAAAA AAAAAAAAAA AAAAA              991
```

(2) INFORMATION FOR SEQ ID NO:20:

(i) SEQUENCE CHARACTERISTICS:
        (A) LENGTH: 253 amino acids
        (B) TYPE: amino acid
        (D) TOPOLOGY: linear (ii) MOLECULE TYPE: protein (xi) SEQUENCE DESCRIPTION: SEQ ID NO:20:

```
Met Pro Ala Ser Met Gly Gly Pro Ala Leu Leu Trp Leu Ala
 1               5                  10

Leu Leu Leu Ser Ser Pro Gly Val Met Ser Ser Asp Thr Leu
15                  20                  25

Lys Pro Thr Val Ser Met Asn Pro Trp Asn Thr Ile Leu
    30                  35                  40

Lys Asp Asp Ser Val Thr Leu Thr Cys Thr Gly Asn Asn Ser
        45                  50                  55

Leu Glu Val Asp Ser Ala Val Trp Leu His Asn Asn Thr Thr
            60                  65                  70

Leu Gln Glu Thr Thr Ser Arg Leu Asp Ile Asn Lys Ala Gln
                75                  80

Ile Gln Asp Ser Gly Glu Tyr Arg Cys Arg Glu Asn Arg Ser
85                  90                  95

Ile Leu Ser Asp Pro Val Tyr Leu Thr Val Phe Thr Glu Trp
    100                 105                 110

Leu Ile Leu Gln Ala Ser Ala Asn Val Val Met Glu Gly Glu
        115                 120                 125

Ser Phe Leu Ile Arg Cys His Ser Trp Lys Asn Leu Arg Leu
            130                 135                 140

Thr Lys Val Thr Tyr Tyr Lys Asp Gly Ile Pro Ile Arg Tyr
                145                 150

Trp Tyr Glu Asn Phe Asn Ile Ser Ile Ser Asn Val Thr Thr
155                 160                 165

Lys Asn Ser Gly Asn Tyr Ser Cys Ser Gly Gln Ile Gln Gln
    170                 175                 180

Lys Gly Tyr Thr Ser Lys Val Leu Asn Ile Ile Val Lys Lys
        185                 190                 195

Glu Pro Thr Lys Gln Asn Lys Tyr Ser Gly Leu Gln Phe Leu
            200                 205                 210

Ile Pro Leu Val Val Val Ile Leu Phe Ala Val Asp Thr Gly
                215                 220

Leu Phe Ile Ser Thr Lys Gln Gln Leu Thr Val Leu Leu Gln
225                 230                 235

Ile Lys Arg Thr Arg Lys Asn Lys Lys Pro Glu Pro Gly Lys
    240                 245                 250

Asn
```

(2) INFORMATION FOR SEQ ID NO:21:

(i) SEQUENCE CHARACTERISTICS:
        (A) LENGTH: 991 nucleotides
        (B) TYPE: nucleic acid

```
        (C) STRANDEDNESS: single
        (D) TOPOLOGY: linear (ii) MOLECULE TYPE: cDNA (xi) SEQUENCE DESCRIPTION: SEQ ID NO:21:

TTTTTTTTTT TTTTTTTTTA TTTATCTAAC TGCCGTTTAT TGAGCACCTA              50

CTATCACATG CCACTTAATC AGTTTGAGTT GGTTGAATGA AGCAGTTCTG             100

CAAAGCCATG ACTGCAGACC TTCCCGTGTG CATCGTGAGC TGCGTCTGAC             150

GATGGAGAAG CGATTGCTGA TGCTGATGTT TCTTAAGCAG CGGCATCAGT             200

TCTTTCCGGG TTCTGGCTTT TTGTTCTTCC TGGTCCTCTT AATCTGCAAG             250

AGCACTGTCA ACTGCTGCTT GGTCGAGATA AACAGTCCTG TGTCCACAGC             300

AAACAGAATC ACCACCACCA ACGGGATCAG GAATTGTAGC CCGGAGTACT             350

TGTTTTGCTT GGTGGGCTCT TTTTTCACAA TAATGTTGAG GACTTTAGAG             400

GTGTAGCCTT TCTGCTGGAT CTGGCCTGAG CAGGAATAGT TGCCGCTGTT             450

TTTGGTTGTG ACGTTGCTAA TGGAGATGTT GAAGTTCTCG TACCAGTACC             500

TGATGGGGAT GCCATCCTTG TAGTAGGTCA CCTTTGTGAG CCTCAAATTC             550

TTCCAACTAT GGCACCTGAT GAGGAAGCTC TCACCCTCCA TCACCACGTT             600

GGCAGAGGCT TGAAGGATCA GCCACTCTGT GAAGACTGTT AGGTACACAG             650

GATCACTCAG GATGGATCTA TTTTCCCGAC ACCTGTACTC CCCACTGTCC             700

TGGATTTGGG CTTTATTGAT GTCCAAACGT GAAGTCGTCT CTTGCAAAGT             750

AGTGTTGTTG TGGAGCCACA CAGCAGAGTC GACTTCAAGG GAGTTGTTCC             800

CAGTACATGT AAGAGTCACA CTGTCATCCT TCAATATTGT ATTCCATGGC             850

GGGTTCATGG ACACTGTAGG TTTCAAGGTA TCTGATGACA TGACACCTGG             900

AGAGGAGAGC AGCAGCGCTA GCCACAGCAG GGCAGGGCCT CCCATGGAAG             950

CAGGCATCTC CTCGTGGCCC CCACGTACGA CTGGACTGGA G                     991

(2) INFORMATION FOR SEQ ID NO:22:

(i) SEQUENCE CHARACTERISTICS:
        (A) LENGTH: 759 nucleotides
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..759

(xi) SEQUENCE DESCRIPTION: SEQ ID NO:22:

ATG CCT GCT TCC ATG GGA GGC CCT GCC CTG CTG TGG CTA GCG              42
Met Pro Ala Ser Met Gly Gly Pro Ala Leu Leu Trp Leu Ala
1               5                  10

CTG CTC CTC TCC TCT CCA GGT GTC ATG TCA TCA GAT ACC TTG              84
Leu Leu Leu Ser Ser Pro Gly Val Met Ser Ser Asp Thr Leu
15                  20                  25

AAA CCT ACA GTG TCC ATG AAC CCG CCA TGG AAT ACA ATA TTG             126
Lys Pro Thr Val Ser Met Asn Pro Pro Trp Asn Thr Ile Leu
30                  35                  40

AAG GAT GAC AGT GTG ACT CTT ACA TGT ACT GGG AAC AAC TCC             168
Lys Asp Asp Ser Val Thr Leu Thr Cys Thr Gly Asn Asn Ser
45                  50                  55
```

```
CTT GAA GTC GAC TCT GCT GTG TGG CTC CAC AAC AAC ACT ACT          210
Leu Glu Val Asp Ser Ala Val Trp Leu His Asn Asn Thr Thr
 60              65                  70

TTG CAA GAG ACG ACT TCA CGT TTG GAC ATC AAT AAA GCC CAA          252
Leu Gln Glu Thr Thr Ser Arg Leu Asp Ile Asn Lys Ala Gln
 75              80

ATC CAG GAC AGT GGG GAG TAC AGG TGT CGG GAA AAT AGA TCC          294
Ile Gln Asp Ser Gly Glu Tyr Arg Cys Arg Glu Asn Arg Ser
 85              90                  95

ATC CTG AGT GAT CCT GTG TAC CTA ACA GTC TTC ACA GAG TGG          336
Ile Leu Ser Asp Pro Val Tyr Leu Thr Val Phe Thr Glu Trp
100             105                 110

CTG ATC CTT CAA GCC TCT GCC AAC GTG GTG ATG GAG GGT GAG          378
Leu Ile Leu Gln Ala Ser Ala Asn Val Val Met Glu Gly Glu
115             120                 125

AGC TTC CTC ATC AGG TGC CAT AGT TGG AAG AAT TTG AGG CTC          420
Ser Phe Leu Ile Arg Cys His Ser Trp Lys Asn Leu Arg Leu
130             135                 140

ACA AAG GTG ACC TAC TAC AAG GAT GGC ATC CCC ATC AGG TAC          462
Thr Lys Val Thr Tyr Tyr Lys Asp Gly Ile Pro Ile Arg Tyr
145             150

TGG TAC GAG AAC TTC AAC ATC TCC ATT AGC AAC GTC ACA ACC          504
Trp Tyr Glu Asn Phe Asn Ile Ser Ile Ser Asn Val Thr Thr
155             160                 165

AAA AAC AGC GGC AAC TAT TCC TGC TCA GGC CAG ATC CAG CAG          546
Lys Asn Ser Gly Asn Tyr Ser Cys Ser Gly Gln Ile Gln Gln
170             175                 180

AAA GGC TAC ACC TCT AAA GTC CTC AAC ATT ATT GTG AAA AAA          588
Lys Gly Tyr Thr Ser Lys Val Leu Asn Ile Ile Val Lys Lys
185             190                 195

GAG CCC ACC AAG CAA AAC AAG TAC TCC GGG CTA CAA TTC CTG          630
Glu Pro Thr Lys Gln Asn Lys Tyr Ser Gly Leu Gln Phe Leu
200             205                 210

ATC CCG TTG GTG GTG GTG ATT CTG TTT GCT GTG GAC ACA GGA          672
Ile Pro Leu Val Val Val Ile Leu Phe Ala Val Asp Thr Gly
215             220

CTG TTT ATC TCG ACC AAG CAG CAG TTG ACA GTG CTC TTG CAG          714
Leu Phe Ile Ser Thr Lys Gln Gln Leu Thr Val Leu Leu Gln
225             230                 235

ATT AAG AGG ACC AGG AAG AAC AAA AAG CCA GAA CCC GGA AAG          756
Ile Lys Arg Thr Arg Lys Asn Lys Lys Pro Glu Pro Gly Lys
240             245                 250

AAC                                                              759
Asn (2) INFORMATION FOR SEQ ID NO:23:

(i) SEQUENCE CHARACTERISTICS:
        (A) LENGTH: 759 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:23:

GTTCTTTCCG GGTTCTGGCT TTTTGTTCTT CCTGGTCCTC TTAATCTGCA            50

AGAGCACTGT CAACTGCTGC TTGGTCGAGA TAAACAGTCC TGTGTCCACA           100

GCAAACAGAA TCACCACCAC CAACGGGATC AGGAATTGTA GCCCGGAGTA           150
```

```
CTTGTTTTGC TTGGTGGGCT CTTTTTTCAC AATAATGTTG AGGACTTTAG          200

AGGTGTAGCC TTTCTGCTGG ATCTGGCCTG AGCAGGAATA GTTGCCGCTG          250

TTTTTGGTTG TGACGTTGCT AATGGAGATG TTGAAGTTCT CGTACCAGTA          300

CCTGATGGGG ATGCCATCCT TGTAGTAGGT CACCTTTGTG AGCCTCAAAT          350

TCTTCCAACT ATGGCACCTG ATGAGGAAGC TCTCACCCTC CATCACCACG          400

TTGGCAGAGG CTTGAAGGAT CAGCCACTCT GTGAAGACTG TTAGGTACAC          450

AGGATCACTC AGGATGGATC TATTTTCCCG ACACCTGTAC TCCCCACTGT          500

CCTGGATTTG GGCTTTATTG ATGTCCAAAC GTGAAGTCGT CTCTTGCAAA          550

GTAGTGTTGT TGTGGAGCCA CACAGCGAG TCGACTTCAA GGGAGTTGTT           600

CCCAGTACAT GTAAGAGTCA CACTGTCATC CTTCAATATT GTATTCCATG          650

GCGGGTTCAT GGACACTGTA GGTTTCAAGG TATCTGATGA CATGACACCT          700

GGAGAGGAGA GCAGCAGCGC TAGCCACAGC AGGGCAGGGC CTCCCATGGA          750

AGCAGGCAT                                                       759
```

(2) INFORMATION FOR SEQ ID NO:24:

(i) SEQUENCE CHARACTERISTICS:
        (A) LENGTH: 229 amino acids
        (B) TYPE: amino acid
        (D) TOPOLOGY: linear (ii) MOLECULE TYPE: protein (xi) SEQUENCE DESCRIPTION: SEQ ID NO:24:

```
Ser Asp Thr Leu Lys Pro Thr Val Ser Met Asn Pro Pro Trp
 1               5                  10

Asn Thr Ile Leu Lys Asp Asp Ser Val Thr Leu Thr Cys Thr
15                  20                  25

Gly Asn Asn Ser Leu Glu Val Asp Ser Ala Val Trp Leu His
        30                  35                  40

Asn Asn Thr Thr Leu Gln Glu Thr Thr Ser Arg Leu Asp Ile
            45                  50                  55

Asn Lys Ala Gln Ile Gln Asp Ser Gly Glu Tyr Arg Cys Arg
                60                  65                  70

Glu Asn Arg Ser Ile Leu Ser Asp Pro Val Tyr Leu Thr Val
                    75                  80

Phe Thr Glu Trp Leu Ile Leu Gln Ala Ser Ala Asn Val Val
85                  90                  95

Met Glu Gly Glu Ser Phe Leu Ile Arg Cys His Ser Trp Lys
    100                 105                 110

Asn Leu Arg Leu Thr Lys Val Thr Tyr Tyr Lys Asp Gly Ile
        115                 120                 125

Pro Ile Arg Tyr Trp Tyr Glu Asn Phe Asn Ile Ser Ile Ser
            130                 135                 140

Asn Val Thr Thr Lys Asn Ser Gly Asn Tyr Ser Cys Ser Gly
                145                 150

Gln Ile Gln Gln Lys Gly Tyr Thr Ser Lys Val Leu Asn Ile
155                 160                 165

Ile Val Lys Lys Glu Pro Thr Lys Gln Asn Lys Tyr Ser Gly
    170                 175                 180

Leu Gln Phe Leu Ile Pro Leu Val Val Ile Leu Phe Ala
        185                 190                 195
```

```
Val Asp Thr Gly Leu Phe Ile Ser Thr Lys Gln Gln Leu Thr
        200                 205                 210

Val Leu Leu Gln Ile Lys Arg Thr Arg Lys Asn Lys Lys Pro
            215                 220

Glu Pro Gly Lys Asn
225
```

(2) INFORMATION FOR SEQ ID NO:25:

(i) SEQUENCE CHARACTERISTICS:
        (A) LENGTH: 33 nucleotides
        (B) TYPE: nucleic acid
        (C) STRANDEDNESS: single
        (D) TOPOLOGY: linear (ii) MOLECULE TYPE: primer (xi) SEQUENCE DESCRIPTION: SEQ ID NO:25:

GCGAAGATCT ATAAATATGC CTGCTTCCAT GGG                                33

(2) INFORMATION FOR SEQ ID NO:26:

(i) SEQUENCE CHARACTERISTICS:
        (A) LENGTH: 33 nucleotides
        (B) TYPE: nucleic acid
        (C) STRANDEDNESS: single
        (D) TOPOLOGY: linear (ii) MOLECULE TYPE: primer (xi) SEQUENCE DESCRIPTION: SEQ ID NO:26:

GCAGGAATTC TTACTCTTTT TTCACAATAA TGT                                33

(2) INFORMATION FOR SEQ ID NO:27:

(i) SEQUENCE CHARACTERISTICS:
        (A) LENGTH: 591 nucleotides
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..591

(xi) SEQUENCE DESCRIPTION: SEQ ID NO:27:

```
ATG CCT GCT TCC ATG GGA GGC CCT GCC CTG CTG TGG CTA GCG         42
Met Pro Ala Ser Met Gly Gly Pro Ala Leu Leu Trp Leu Ala
 1               5                  10

CTG CTG CTC TCC TCT CCA GGT GTC ATG TCA TCA GAT ACC TTG         84
Leu Leu Leu Ser Ser Pro Gly Val Met Ser Ser Asp Thr Leu
15                  20                  25

AAA CCT ACA GTG TCC ATG AAC CCG CCA TGG AAT ACA ATA TTG        126
Lys Pro Thr Val Ser Met Asn Pro Pro Trp Asn Thr Ile Leu
            30                  35                  40

AAG GAT GAC AGT GTG ACT CTT ACA TGT ACT GGG AAC AAC TCC        168
Lys Asp Asp Ser Val Thr Leu Thr Cys Thr Gly Asn Asn Ser
                45                  50                  55

CTT GAA GTC GAC TCT GCT GTG TGG CTC CAC AAC AAC ACT ACT        210
Leu Glu Val Asp Ser Ala Val Trp Leu His Asn Asn Thr Thr
                    60                  65                  70

TTG CAA GAG ACG ACT TCA CGT TTG GAC ATC AAT AAA GCC CAA        252
Leu Gln Glu Thr Thr Ser Arg Leu Asp Ile Asn Lys Ala Gln
```

```
                    75                      80
ATC CAG GAC AGT GGG GAG TAC AGG TGT CGG GAA AAT AGA TCC          294
Ile Gln Asp Ser Gly Glu Tyr Arg Cys Arg Glu Asn Arg Ser
 85                  90                      95

ATC CTG AGT GAT CCT GTG TAC CTA ACA GTC TTC ACA GAG TGG          336
Ile Leu Ser Asp Pro Val Tyr Leu Thr Val Phe Thr Glu Trp
    100                 105                 110

CTG ATC CTT CAA GCC TCT GCC AAC GTG GTG ATG GAG GGT GAG          378
Leu Ile Leu Gln Ala Ser Ala Asn Val Val Met Glu Gly Glu
            115                 120                 125

AGC TTC CTC ATC AGG TGC CAT AGT TGG AAG AAT TTG AGG CTC          420
Ser Phe Leu Ile Arg Cys His Ser Trp Lys Asn Leu Arg Leu
                130                 135                 140

ACA AAG GTG ACC TAC TAC AAG GAT GGC ATC CCC ATC AGG TAC          462
Thr Lys Val Thr Tyr Tyr Lys Asp Gly Ile Pro Ile Arg Tyr
                    145                 150

TGG TAC GAG AAC TTC AAC ATC TCC ATT AGC AAC GTC ACA ACC          504
Trp Tyr Glu Asn Phe Asn Ile Ser Ile Ser Asn Val Thr Thr
155                 160                 165

AAA AAC AGC GGC AAC TAT TCC TGC TCA GGC CAG ATC CAG CAG          546
Lys Asn Ser Gly Asn Tyr Ser Cys Ser Gly Gln Ile Gln Gln
        170                 175                 180

AAA GGC TAC ACC TCT AAA GTC CTC AAC ATT ATT GTG AAA AAA          588
Lys Gly Tyr Thr Ser Lys Val Leu Asn Ile Ile Val Lys Lys
                185                 190                 195

GAG                                                              591
Glu (2) INFORMATION FOR SEQ ID NO:28:

(i) SEQUENCE CHARACTERISTICS:
        (A) LENGTH: 197 amino acids
        (B) TYPE: amino acid
        (D) TOPOLOGY: linear (ii) MOLECULE TYPE: protein (xi) SEQUENCE DESCRIPTION: SEQ ID NO:28:

Met Pro Ala Ser Met Gly Gly Pro Ala Leu Leu Trp Leu Ala
 1               5                      10

Leu Leu Leu Ser Ser Pro Gly Val Met Ser Ser Asp Thr Leu
15                  20                  25

Lys Pro Thr Val Ser Met Asn Pro Pro Trp Asn Thr Ile Leu
    30                  35                  40

Lys Asp Asp Ser Val Thr Leu Thr Cys Thr Gly Asn Asn Ser
            45                  50                  55

Leu Glu Val Asp Ser Ala Val Trp Leu His Asn Asn Thr Thr
                60                  65                  70

Leu Gln Glu Thr Thr Ser Arg Leu Asp Ile Asn Lys Ala Gln
                    75                  80

Ile Gln Asp Ser Gly Glu Tyr Arg Cys Arg Glu Asn Arg Ser
 85                  90                      95

Ile Leu Ser Asp Pro Val Tyr Leu Thr Val Phe Thr Glu Trp
    100                 105                 110

Leu Ile Leu Gln Ala Ser Ala Asn Val Val Met Glu Gly Glu
            115                 120                 125

Ser Phe Leu Ile Arg Cys His Ser Trp Lys Asn Leu Arg Leu
                130                 135                 140
```

```
Thr Lys Val Thr Tyr Tyr Lys Asp Gly Ile Pro Ile Arg Tyr
            145                 150

Trp Tyr Glu Asn Phe Asn Ile Ser Ile Ser Asn Val Thr Thr
155             160                 165

Lys Asn Ser Gly Asn Tyr Ser Cys Ser Gly Gln Ile Gln Gln
        170                 175                 180

Lys Gly Tyr Thr Ser Lys Val Leu Asn Ile Ile Val Lys Lys
        185                 190                 195

Glu
```

(2) INFORMATION FOR SEQ ID NO:29:

(i) SEQUENCE CHARACTERISTICS:
        (A) LENGTH: 591 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:29:

```
CTCTTTTTTC ACAATAATGT TGAGGACTTT AGAGGTGTAG CCTTTCTGCT          50
GGATCTGGCC TGAGCAGGAA TAGTTGCCGC TGTTTTTGGT TGTGACGTTG         100
CTAATGGAGA TGTTGAAGTT CTCGTACCAG TACCTGATGG GGATGCCATC         150
CTTGTAGTAG GTCACCTTTG TGAGCCTCAA ATTCTTCCAA CTATGGCACC         200
TGATGAGGAA GCTCTCACCC TCCATCACCA CGTTGGCAGA GGCTTGAAGG         250
ATCAGCCACT CTGTGAAGAC TGTTAGGTAC ACAGGATCAC TCAGGATGGA         300
TCTATTTTCC CGACACCTGT ACTCCCCACT GTCCTGGATT TGGGCTTTAT         350
TGATGTCCAA ACGTGAAGTC GTCTCTTGCA AGTAGTGTT GTTGTGGAGC          400
CACACAGCAG AGTCGACTTC AAGGGAGTTG TTCCCAGTAC ATGTAAGAGT         450
CACACTGTCA TCCTTCAATA TTGTATTCCA TGGCGGGTTC ATGGACACTG         500
TAGGTTTCAA GGTATCTGAT GACATGACAC CTGGAGAGGA GAGCAGCAGC         550
GCTAGCCACA GCAGGGCAGG GCCTCCCATG GAAGCAGGCA T                  591
```

(2) INFORMATION FOR SEQ ID NO:30:

(i) SEQUENCE CHARACTERISTICS:
        (A) LENGTH: 687 nucleotides
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..687

(xi) SEQUENCE DESCRIPTION: SEQ ID NO:30:

```
TCA GAT ACC TTG AAA CCT ACA GTG TCC ATG AAC CCG CCA TGG         42
Ser Asp Thr Leu Lys Pro Thr Val Ser Met Asn Pro Pro Trp
 1               5                  10

AAT ACA ATA TTG AAG GAT GAC AGT GTG ACT CTT ACA TGT ACT         84
Asn Thr Ile Leu Lys Asp Asp Ser Val Thr Leu Thr Cys Thr
15              20                  25

GGG AAC AAC TCC CTT GAA GTC GAC TCT GCT GTG TGG CTC CAC        126
Gly Asn Asn Ser Leu Glu Val Asp Ser Ala Val Trp Leu His
        30                  35                  40
```

```
AAC AAC ACT ACT TTG CAA GAG ACG ACT TCA CGT TTG GAC ATC                168
Asn Asn Thr Thr Leu Gln Glu Thr Thr Ser Arg Leu Asp Ile
         45                  50                  55

AAT AAA GCC CAA ATC CAG GAC AGT GGG GAG TAC AGG TGT CGG                210
Asn Lys Ala Gln Ile Gln Asp Ser Gly Glu Tyr Arg Cys Arg
             60                  65                  70

GAA AAT AGA TCC ATC CTG AGT GAT CCT GTG TAC CTA ACA GTC                252
Glu Asn Arg Ser Ile Leu Ser Asp Pro Val Tyr Leu Thr Val
                 75                  80

TTC ACA GAG TGG CTG ATC CTT CAA GCC TCT GCC AAC GTG GTG                294
Phe Thr Glu Trp Leu Ile Leu Gln Ala Ser Ala Asn Val Val
85                  90                  95

ATG GAG GGT GAG AGC TTC CTC ATC AGG TGC CAT AGT TGG AAG                336
Met Glu Gly Glu Ser Phe Leu Ile Arg Cys His Ser Trp Lys
    100                 105                 110

AAT TTG AGG CTC ACA AAG GTG ACC TAC TAC AAG GAT GGC ATC                378
Asn Leu Arg Leu Thr Lys Val Thr Tyr Tyr Lys Asp Gly Ile
        115                 120                 125

CCC ATC AGG TAC TGG TAC GAG AAC TTC AAC ATC TCC ATT AGC                420
Pro Ile Arg Tyr Trp Tyr Glu Asn Phe Asn Ile Ser Ile Ser
            130                 135                 140

AAC GTC ACA ACC AAA AAC AGC GGC AAC TAT TCC TGC TCA GGC                462
Asn Val Thr Thr Lys Asn Ser Gly Asn Tyr Ser Cys Ser Gly
                145                 150

CAG ATC CAG CAG AAA GGC TAC ACC TCT AAA GTC CTC AAC ATT                504
Gln Ile Gln Gln Lys Gly Tyr Thr Ser Lys Val Leu Asn Ile
155                 160                 165

ATT GTG AAA AAA GAG CCC ACC AAG CAA AAC AAG TAC TCC GGG                546
Ile Val Lys Lys Glu Pro Thr Lys Gln Asn Lys Tyr Ser Gly
    170                 175                 180

CTA CAA TTC CTG ATC CCG TTG GTG GTG GTG ATT CTG TTT GCT                588
Leu Gln Phe Leu Ile Pro Leu Val Val Val Ile Leu Phe Ala
        185                 190                 195

GTG GAC ACA GGA CTG TTT ATC TCG ACC AAG CAG CAG TTG ACA                630
Val Asp Thr Gly Leu Phe Ile Ser Thr Lys Gln Gln Leu Thr
            200                 205                 210

GTG CTC TTG CAG ATT AAG AGG ACC AGG AAG AAC AAA AAG CCA                672
Val Leu Leu Gln Ile Lys Arg Thr Arg Lys Asn Lys Lys Pro
                215                 220

GAA CCC GGA AAG AAC                                                    687
Glu Pro Gly Lys Asn
225
```

(2) INFORMATION FOR SEQ ID NO:31:

(i) SEQUENCE CHARACTERISTICS:
        (A) LENGTH: 173 amino acids
        (B) TYPE: amino acid
        (D) TOPOLOGY: linear (ii) MOLECULE TYPE: protein (xi) SEQUENCE DESCRIPTION: SEQ ID NO:31:

```
Ser Asp Thr Leu Lys Pro Thr Val Ser Met Asn Pro Pro Trp
1               5                   10

Asn Thr Ile Leu Lys Asp Asp Ser Val Thr Leu Thr Cys Thr
15                  20                  25

Gly Asn Asn Ser Leu Glu Val Asp Ser Ala Val Trp Leu His
    30                  35                  40

Asn Asn Thr Thr Leu Gln Glu Thr Thr Ser Arg Leu Asp Ile
```

-continued

```
            45                  50                  55
Asn Lys Ala Gln Ile Gln Asp Ser Gly Glu Tyr Arg Cys Arg
            60                  65                  70

Glu Asn Arg Ser Ile Leu Ser Asp Pro Val Tyr Leu Thr Val
            75                  80

Phe Thr Glu Trp Leu Ile Leu Gln Ala Ser Ala Asn Val Val
85                  90                  95

Met Glu Gly Glu Ser Phe Leu Ile Arg Cys His Ser Trp Lys
    100                 105                 110

Asn Leu Arg Leu Thr Lys Val Thr Tyr Tyr Lys Asp Gly Ile
            115                 120                 125

Pro Ile Arg Tyr Trp Tyr Glu Asn Phe Asn Ile Ser Ile Ser
            130                 135                 140

Asn Val Thr Thr Lys Asn Ser Gly Asn Tyr Ser Cys Ser Gly
                145                 150

Gln Ile Gln Gln Lys Gly Tyr Thr Ser Lys Val Leu Asn Ile
155                 160                 165

Ile Val Lys Lys Glu
170
```

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. A method to detect canine IgE comprising:
   (a) contacting an isolated canine $Fc_\epsilon$ receptor ($Fc_\epsilon R$) molecule with a putative canine IgE-containing composition under conditions suitable for formation of a $Fc_\epsilon R$ molecule:IgE complex; and
   (b) determining the presence of IgE by detecting said $Fc_\epsilon R$ molecule:IgE complex, the presence of said $Fc_\epsilon R$ molecule:IgE complex indicating the presence of IgE, wherein said canine $Fc_\epsilon R$ molecule comprises a protein having an amino acid sequence selected from the group consisting of SEQ ID NO: 4, SEQ ID NO: 9, SEQ TD NO: 14, SEQ ID NO: 20, SEQ ID NO: 24, SEQ ID NO: 28 and SEQ ID NO: 31.

2. The method of claim 1, wherein said canine FcεR molecule is encoded by a nucleic acid molecule selected from the group consisting of ncFcεRα1$_{609}$, ncFcεRα1$_{591}$, ncFcεRα2$_{609}$, ncFcεRα2$_{591}$, ncFcεRα3$_{617}$, ncFcεRα3$_{597}$, ncFcεRα4$_{591}$, ncFcεRα4$_{687}$, ncFcεRα4$_{991}$, ncFcεRα4$_{759}$.

3. The method of claim 1, wherein said canine $Fc_\epsilon R$ molecule is encoded by a nucleic acid molecule selected from the group consisting of: (a) a nucleic acid molecule comprising a nucleic acid sequence selected from the group consisting of SEQ ID NO: 3, SEQ ID NO: 6, SEQ ID NO: 8, SEQ ID NO: 11, SEQ ID NO: 13, SEQ ID NO: 16, SEQ ID NO: 19, SEQ ID NO: 22, SEQ ID NO: 27 and SEQ ID NO: 30.

4. The method of claim 1, wherein said canine $Fc_\epsilon R$ molecule is conjugated to a detectable marker.

5. The method of claim 1, wherein said canine $Fc_\epsilon R$ molecule is conjugated to a detectable marker selected from the group consisting of a radioactive label, a fluorescent label, a chemiluminescent label, a chromophoric label and a ligand.

6. The method of claim 1, wherein said putative canine IgE-containing composition comprises a bodily fluid selected from the group consisting of serum, blood and plasma.

7. The method of claim 1 further comprising the step selected from the group consisting of:
   (a) immobilizing said canine $Fc_\epsilon R$ molecule to a substrate prior to performing stop (a) to form a $Fc_\epsilon R$ molecule-coated substrate; and
   (b) immobilizing said putative IgE-containing composition to a substrate prior to performing step (a) to form a putative IgE-containing composition-coated substrate, wherein said substrate is uncoated and directly binds said canine IgE or is coated with antigen or is coated with an anti-IgE antibody which specifically binds said canine IgE.

8. The method of claim 7, wherein said antigen is selected from the group consisting of an allergen and a parasitic antigen.

9. The method of claim 7, further comprising a step of removing unbound material from said substrate prior to performing step (b).

10. The method of claim 7, wherein said substrate is selected from the group consisting of a dipstick, a microtiter plate, a bead, an immunoblot membrane and an immunoblot paper.

11. The method of claim 1, wherein said step of determining comprises performing an assay selected from the group consisting of an enzyme-linked immunoassay, a radioimmunoassay, an immunoprecipitation, a fluorescence immunoassay, a chemiluminescent assay, an immunoblot assay, a lateral flow assay, an agglutination assay and a particulate-based assay.

12. The method of claim 1, wherein said step of detecting comprises:
   (a) contacting said canine $Fc_\epsilon R$ molecule:IgE complex with an indicator molecule that binds selectively to said $Fc_\epsilon R$ molecule:IgE complex;
   (b) removing excess amounts of said indicator molecule that do not selectively bind to said $Fc_\epsilon R$ molecule:IgE complex; and
   (c) detecting said indicator molecule, wherein presence of said indicator molecule is indicative of the presence of said canine IgE.

13. The method of claim 12, wherein said indicator molecule comprises a compound selected from the group consisting of a $Fc_\epsilon R$ molecule, an antigen, an antibody and a lectin.

14. The method of claim 1, said method comprising the steps of:
   (a) immobilizing said canine $Fc_\epsilon R$ molecule on a substrate;
   (b) contacting said canine $Fc_\epsilon R$ molecule with said putative IgE-containing composition under conditions suitable for formation of a $Fc_\epsilon R$ molecule:IgE complex bound to said substrate;
   (c) removing unbound material from said substrate under conditions that retain said $Fc_\epsilon R$ molecule:IgE complex binding to said substrate; and
   (d) detecting the presence of said $Fc_\epsilon R$ molecule:IgE complex.

15. The method of claim 14, wherein the presence of said $Fc_\epsilon R$ molecule:IgE complex is detected by contacting said $Fc_\epsilon R$ molecule:IgE complex with a compound selected from the group consisting of an antigen and an antibody that binds selectively to said IgE.

16. The method of claim 14, wherein said compound comprises a detectable marker.

17. The method of claim 1, said method comprising the steps of:
   (a) immobilizing a desired antigen on a substrate;
   (b) contacting said antigen with said putative IgE-containing composition under conditions suitable for formation of an antigen:IgE complex bound to said substrate;
   (c) removing unbound material from said substrate under conditions that retain said antigen:IgE complex binding to said substrate; and
   (d) detecting the presence of said antigen:IgE complex by contacting said antigen:IgE complex with said canine $Fc_\epsilon R$ molecule.

18. The method of claim 1, said method comprising the steps of:
   (a) immobilizing ail antibody that binds selectively to IgE on a substrate;
   (b) contacting said antibody with said putative IgE-containing composition under conditions suitable for formation of an antibody:IgE complex bound to said substrate;
   (e) removing unbound material from said substrate under conditions that retain said antibody:IgE complex binding to said substrate; and
   (d) detecting the presence of said antibody:IgE complex by contacting said antibody:IgE complex with said canine $Fc_\epsilon R$ molecule.

19. The method of claim 1, said method comprising the steps of:
   (a) immobilizing said putative IgE-containing composition on a substrate;
   (b) contacting said composition with said canine $Fc_\epsilon R$ molecule under conditions suitable for formation of a $Fc_\epsilon R$ molecule:IgE complex bound to said substrate;
   (e) removing unbound material from said substrate under conditions that retain said $Fc_\epsilon R$ molecule:IgE complex binding to said substrate; and
   (d) detecting the presence of said $Fc_\epsilon R$ molecule:IgE complex.

20. The method of claim 19, wherein said canine $Fc_\epsilon R$ molecule comprises a detectable marker.

21. A kit for detecting canine IgE comprising a canine $Fc_\epsilon R$ molecule having an amino acid sequence selected from the group consisting of SEQ ID NO: 4, SEQ ID NO: 9, SEQ ID NO: 14, SEQ ID NO: 20, SEQ ID NO: 24, SEQ ID NO: 28 and SEQ ID NO: 31.

22. The kit of claim 21, wherein said detection means further comprises an antigen selected from the group consisting of an allergen and a parasite antigen, wherein said antigen induces IgE antibody production in canids.

23. The kit of claim 22, wherein said antigen is immobilized on a substrate.

24. The kit of claim 23, wherein said substrate is selected from the group consisting of a dipstick, a microtiter plate, a bead, all immunoblot membrane and an immunoblot paper.

25. The kit of claim 23, wherein said substrate is latex beads.

26. The kit of claim 22, wherein said allergen is derived from material selected from the group consisting of fungi, trees, weeds, shrubs, grasses, wheat, corn, soybean, rice, eggs, milk, cheese, bovine, poultry, swine, sheep, yeast, fleas, flies, mosquitos, mites, midges, biting gnats, lice, bees, wasps, ants, true bugs and ticks.

27. The kit of claim 26, wherein said flea allergen is a flea saliva antigen.

28. The kit of claim 22, wherein said parasite antigen is a heartworm antigen.

29. The kit of claim 21, wherein said detection means comprises an antibody that selectively binds to said canine IgE.

30. The kit of claim 21, wherein said detection means detects said canine $Fc_\epsilon R$ molecule.

31. The kit of claim 21, wherein said canine FcεR molecule is encoded by a nucleic acid molecule selected from the group consisting of $ncFc\epsilon R\alpha 1_{609}$, $ncFc\epsilon R\alpha 1_{591}$, $ncFc\epsilon R\alpha 2_{609}$, $ncFc\epsilon R\alpha 2_{591}$, $ncFc\epsilon R\alpha 3_{617}$, $ncFc\epsilon R\alpha 3_{597}$, $ncFc\epsilon R\alpha 4_{591}$, $ncFc\epsilon R\alpha 4_{687}$, $ncFc\epsilon R\alpha 4_{991}$, $ncFc\epsilon R\alpha 4_{759}$.

32. The kit of claim 21, wherein said canine $Fc_\epsilon R$ molecule is encoded by a nucleic acid molecule selected from the group consisting of a nucleic acid molecule comprising a nucleic acid sequence selected from the group consisting of: (a) a nucleic acid molecule comprising a nucleic acid sequence selected from the group consisting of SEQ ID NO: 3, SEQ ID NO: 6, SEQ ID NO: 8, SEQ ID NO: 11, SEQ ID NO: 13, SEQ ID NO: 16, SEQ ID NO: 19, SEQ ID NO: 22, SEQ ID NO: 27 and SEQ ID NO: 30.

33. The kit of claim 21, wherein said canine $Fc_\epsilon R$ molecule is conjugated to a detectable marker.

34. The kit of claim 21, wherein said canine $Fc_\epsilon R$ molecule is conjugated to a detectable marker selected from the group consisting of a radioactive label, a fluorescent label, a chemiluminescent label, a chromophoric label and a ligand.

35. The kit of claim 21 further comprising an apparatus comprising:
   (a) a support structure defining a flow path;
   (b) a labeling reagent comprising a bead conjugated to an antigen, wherein said labeling reagent is impregnated within the support structure in a labeling zone; and
   (c) a capture reagent comprising said $Fc_\epsilon R$ molecule, wherein said capture reagent is located downstream of said labeling reagent within a capture zone fluidly connected to said labeling zone in such a manner that said labeling reagent can flow from said labeling zone into said capture zone.

36. The kit of claim 35, wherein said apparatus further comprises a sample receiving zone located upstream of said labeling reagent.

37. The kit of claim 35, wherein said apparatus further comprises an absorbent located at the end of said flow path.

38. The kit of claim 35, wherein said bead is a latex bead.

* * * * *

UNITED STATES PATENT AND TRADEMARK OFFICE
CERTIFICATE OF CORRECTION

PATENT NO. : 6,060,326
DATED : May 9, 2000
INVENTOR(S) : Frank et al.

It is certified that error appears in the above-identified patent and that said Letters Patent is hereby corrected as shown below:

Title page,
Under FOREIGN PATENT DOCUMENTS", insert --
WO 94/29696    12/1994    WIPO
WO 95/16203    6/1995     WIPO
WO 97/20859    6/1997     WIPO --.

Column 63,
Line 43, delete "TD" and insert -- ID --.

Column 64,
Line 31, delete "stop" and insert -- step --.

Column 65,
Line 36, delete "ail" and insert -- an --.

Signed and Sealed this

Twenty-fifth Day of December, 2001

Attest:

JAMES E. ROGAN
Attesting Officer    *Director of the United States Patent and Trademark Office*